(12) United States Patent
Tsukamoto et al.

(10) Patent No.: US 7,398,163 B2
(45) Date of Patent: Jul. 8, 2008

(54) SENSING APPARATUS

(75) Inventors: Nobuo Tsukamoto, Akishima (JP); Kazuo Akaike, Sayama (JP); Tsukasa Kobata, Sayama (JP)

(73) Assignees: Nihon Dempa Kogyo Co., Ltd., Tokyo (JP); DSP Technology Associates, Inc., Tokyo (JP)

( * ) Notice: Subject to any disclaimer, the term of this patent is extended or adjusted under 35 U.S.C. 154(b) by 0 days.

(21) Appl. No.: 11/659,764

(22) PCT Filed: Aug. 11, 2005

(86) PCT No.: PCT/JP2005/015099

§ 371 (c)(1),
(2), (4) Date: May 29, 2007

(87) PCT Pub. No.: WO2006/016721

PCT Pub. Date: Feb. 16, 2006

(65) Prior Publication Data

US 2007/0251322 A1    Nov. 1, 2007

(30) Foreign Application Priority Data

Aug. 11, 2004  (JP) ............................ 2004-234735
Feb. 15, 2005  (JP) ............................ 2005-038205

(51) Int. Cl.
  *G01N 31/00*  (2006.01)
(52) U.S. Cl. .................. 702/32; 73/24.06; 73/31.05; 702/89; 702/177; 702/25; 331/65; 331/158; 331/175; 331/116 R
(58) Field of Classification Search .................. 702/25, 702/32, 89, 177; 331/65, 176, 10, 68, 158, 331/175, 74, 116 R, 116 FE, 108 C; 340/466, 340/467; 324/727, 162; 310/316.01, 317; 361/278, 280; 73/24.06, 31.05

See application file for complete search history.

(56) References Cited

U.S. PATENT DOCUMENTS 4,100,512 A * 7/1978 Valdois et al. ............... 331/158
4,318,063 A * 3/1982 Przyjemski .................. 331/158

(Continued)

FOREIGN PATENT DOCUMENTS

JP        3-140838        6/1991

(Continued)

*Primary Examiner*—Carol S Tsai
(74) *Attorney, Agent, or Firm*—Jordan and Hamburg LLP

(57) ABSTRACT

An object of the present invention is to provide a sensing instrument capable to detect a substance existing in a very small quantity, such as environmental pollutants, instantly with a high degree of precision. As a specific means for solving the problem, a frequency signal from a crystal oscillator is sampled using a frequency signal from a reference clock generating part, the sampling value is outputted in a digital signal, quadrature detection is conducted with the digital signal for a frequency signal corresponding to the output signal, the rotational vector rotating at a frequency corresponding to the difference between the frequency of the frequency signal and the frequency of a sinusoidal wave used for the quadrature detection is taken out, and the variation of the frequency is detected by detecting the velocity of the rotational vector based on the respective sampling values. In addition to that, the measurement range of the variation of frequency can be widened by multiplying the above-described rotational vector by the reversely rotational vector corresponding to the velocity of the rotational vector.

10 Claims, 19 Drawing Sheets

U.S. PATENT DOCUMENTS

| | | | | |
|---|---|---|---|---|
| 4,453,141 | A * | 6/1984 | Rosati | 331/158 |
| 4,588,969 | A * | 5/1986 | Emmons | 331/156 |
| 4,609,885 | A * | 9/1986 | Renoult | 331/158 |
| 4,735,081 | A * | 4/1988 | Luoma et al. | 73/24.06 |
| 4,891,611 | A * | 1/1990 | Frerking | 331/158 |
| 4,949,055 | A * | 8/1990 | Leitl | 331/158 |
| 5,659,271 | A * | 8/1997 | Tanabe | 331/158 |
| 5,777,525 | A * | 7/1998 | Tanabe | 331/158 |
| 5,786,735 | A * | 7/1998 | Su | 331/158 |
| 6,707,346 | B2 * | 3/2004 | Tillotson et al. | 331/175 |
| 7,106,143 | B2 * | 9/2006 | Bloch et al. | 331/65 |
| 2003/0058057 | A1 * | 3/2003 | Schmidt | 331/175 |
| 2003/0112086 | A1 * | 6/2003 | Tillotson et al. | 331/175 |
| 2005/0081635 | A1 | 4/2005 | Kobayashi | |
| 2006/0265176 | A1 * | 11/2006 | Yamauchi et al. | 702/130 |
| 2008/0060438 | A1 * | 3/2008 | Shinbo et al. | 73/579 |

FOREIGN PATENT DOCUMENTS

| | | |
|---|---|---|
| JP | 6-241972 | 9/1994 |
| JP | 6-308009 | 11/1994 |
| JP | 2001-000435 | 1/2001 |
| JP | 2004-279167 | 10/2004 |

\* cited by examiner (a)

OUTPUT OF PULSE WIDTH
CONTROLLING PART (b)

HIGHER BIT SIDE
ADDER INPUT

5 ─────────────────

(c)

ADDER OUTPUT (d)

INTEGRATOR OUTPUT (a)

OUTPUT OF PULSE WIDTH CONTROLLING PART (b)

HIGHER BIT SIDE ADDER INPUT    5 —————————

(c)

ADDER OUTPUT (d)

INTEGRATOR OUTPUT

SENSING APPARATUS

TECHNICAL FIELD

The present invention relates to a sensing instrument for detecting a substance to be detected using a sensor oscillator, for instance, a crystal oscillator, in which an adsorbing layer to adsorb the substance to be detected is formed on the surface thereof, and the natural frequency thereof varies by adsorption of the substance to be detected, and by detecting the variation of the natural frequency of this sensor oscillator.

BACKGROUND ART

The need for knowing the concentrations of various environmental pollutants in rivers and soils in a quest to preserve the environment is increasing and establishment of measurement technology for a very small quantity of pollutant has been demanded because there are some pollutants which are very toxic to humans even the quantity thereof is very small. There is a pollutant named dioxin which recently attracts public attention, and methods to use a gas chromatography mass spectrometer and an ELISA method (enzyme-linked immunosorbent assay) are known as a method to determine this dioxin. The gas chromatography mass analyzer can perform a trace analysis with a high degree of precision in an order of $10^{-12}$ g/ml. However, there are disadvantages in that the price of the instrument is extremely high, which results in a high analysis cost, and a long period of time is necessary for analysis. Though the ELISA method is more inexpensive in analyzer price, and in analysis cost, and faster in required time for analysis, compared with those in the gas chromatography mass analyzer, but a problem is a low analytical precision in the order of $10^{-9}$ g/ml.

Then, the present inventor pays attention to a crystal oscillator as a measuring instrument for pollutant such as dioxin or the like, from the fact that once a substance to be detected is attached to a crystal oscillator, the natural frequency of the crystal oscillator varies according to the amount of the attachment. On the other hand, there is a technology as a chemical sensing instrument using a crystal oscillator, which is described in Patent Document 1. The instrument includes a sampling circuit for outputting the absolute value of a difference frequency between the oscillation frequency of a sensor oscillator and the reference frequency generated by the reference oscillator, a frequency divider circuit dividing the difference frequency by a prescribed frequency divider ratio, a counter for counting the cycle of the frequency divider output using the cycle of the reference frequency as a clock, and a calculating device for determining the oscillation frequency of a sensor oscillator based on the counted cycle, and is for performing the identification of an adsorption gas. Since the chemical sensing instrument determines a difference frequency, it has an advantage of making the absolute value of a frequency to be measured small, and making it possible to perform measurement with a high resolution without enlarging the measurement range.

However, the technology in Patent Document 1 is designed to lower the clock frequency of the counter by using the frequency divider circuit. Accordingly, if the above-described difference frequency is high, the number of stages of the frequency divider circuit increases, which results in increase of the phase noise. Therefore, the above-described difference frequency cannot be made so high practically, which brings a problem of difficulty in assuring a high measurement precision. As a result, the range of application is limited, and it is difficult to apply the technology when detection of a very small quantity of material such as dioxin or the like with a high degree of precision is required. Furthermore, since it uses a counter, there is the problem of lengthy measuring time if a high resolution is required.

Patent Document 1
Japanese Patent Application Laid-open No. Hei 6-241972

DISCLOSURE OF THE INVENTION

The present invention is achieved under the above-described circumstances, and the object thereof is to provide a sensing instrument for detecting a substance to be detected existing in a very small quantity such as environmental pollutant with a high degree of precision. Another object is to provide a sensing instrument which can instantaneously detect a substance to be detected with a high degree of precision. Still another object of the present invention is to provide a sensing instrument which can widen the measurement range when detecting the substance to be detected with a high degree of precision.

A sensing instrument of the present invention is the sensing instrument for detecting a substance to be detected, based on the variation of the natural frequency of a sensor oscillator, using the sensor oscillator, on the surface of which an adsorbing layer to adsorb a substance to be detected is formed, and of which natural frequency is varied by adsorption of the substance to be detected, the apparatus characterized by including:

a sensor oscillator circuit to oscillate the above-described sensor oscillator, a reference clock generating part to generate a clock signal for sampling frequency signals from the above-described sensor oscillator, an analog/digital converting part for sampling the frequency signal from the above-described sensor oscillator by the clock signal from the above-described reference clock generating part, and outputting the sampling value as a digital signal, a means for obtaining a rotational vector to obtain a real part and an imaginary part when performing a quadrature detection with a digital signal for a frequency signal corresponding to the output signal from the analog/digital converting part, and performing complex expression of the rotational vector rotating at an angular velocity corresponding to the difference of frequency between the frequency of the frequency signal and the frequency identified by the digital signal used for the quadrature detection, and a means for calculating the velocity of the rotational vector to determine the angular velocity of the rotational vector based on respective time series data of the above-described actual number portion and the imaginary number portion obtained by the means for obtaining the rotational vector.

The present invention may be structured to include a means for determining the difference between the angular velocity of a rotational vector when the sensor oscillator is placed under a first circumstance and the angular velocity of a rotational vector when the sensor oscillator is placed under a second circumstance. As the first circumstance, for instance, a solvent such as pure water or the like can be cited, and as the second circumstance, the case when the solvent contains a substance to be detected.

The above-described means for obtaining the rotational vector may be structured to include a means for performing a quadrature detection for a frequency signal corresponding to the output signal from the analog/digital converting part, and a means for eliminating high frequency components contained in the data obtained by this means. The above-described means for calculating the velocity of the rotational vector may be structured as a means for determining a frequency variation based on the calculation of $\{Q(n)-Q(n-1)\}\cdot I(n)-\{I(n)-I(n-1)\cdot Q(n)\}$, when the real part and the imaginary part corresponding to the above-described sampling value at a certain timing are taken as $I(n)$ and $Q(n)$ respectively, and a real part and an imaginary part corresponding to the above-described sampling value at a timing earlier than the above timing are taken as $I(n-1)$ and $Q(n-1)$ respectively.

The above-described means for calculating the velocity of the rotational vector may be structured to be provided with a means for determining the average value within a prescribed period of time to the calculated result of the above-described calculation, and as a concrete example, it is structured as a means for determining the moving average. Furthermore, a correction processing part for performing division of the above-described real part and the imaginary part by the scalar of the vector determined by these real part and the imaginary part is preferably provided at a pre-stage of the above-described means for calculating the velocity of the rotational vector.

Further, it is preferable for the present invention to be structured as follows. That is, the present invention further includes:

a reversely rotational vector generating part for generating a real part and an imaginary part when displaying in complex expression of a reversely rotational vector rotating in the opposite direction to the above-described rotational vector at the angular velocity corresponding to a frequency variation determined by the above-described means for calculating the velocity of the rotational vector, and a frequency range correcting part, provided at the pre-stage of the above-described means for calculating the velocity of the rotational vector, and for compensating the range of frequency variation by retarding the angular velocity of the above-described rotational vector by calculating the real part and the imaginary part of the rotational vector obtained by the above-described means for obtaining the rotational vector, and the real part and the imaginary part of the reversely rotational vector generated by the above-described reversely rotational vector generating part.

In this case, the reversely rotational vector generating part can be structured to include a data table in which a set of the real part and the imaginary part defining the position of the reversely rotational vector on the complex surface are arranged in turn along the rotational direction, and an address controlling part for generating a reversely rotational vector by generating the address of the above-described data table using an increment number or a decrement number corresponding to the above-described frequency variation. As a more concrete example, it is possible to cite a structure that the reversely rotational vector generating part includes a pulse width controlling part outputting a pulse train having a duty ratio in accordance with the lower rank bit value when expressing the frequency variation obtained by the above-described means for calculating the velocity of the rotational vector with a digital signal, and an addition part adding the higher rank bit value when expressing the above-described frequency variation with the digital signal and the level of the pulse formed by said pulse width controlling part to output to the above-described address controlling part, in which, the above-described address generating part integrates the output value from the adding part, and the integrated value is used as an address in the above-described data table.

The present invention samples a frequency signal from a sensor oscillator such as, for instance, a crystal oscillator or the like, using a clock signal from a reference clock generating part, outputs the sampling value thereof as a digital signal, performs a quadrature detection for the frequency signal corresponding to the output signal using the digital signal, and obtains a rotational vector rotating at the frequency corresponding to the difference between the frequency of the frequency signal (output signal of the analog/digital converting part) identified by the above-described sampling value and the frequency identified by the digital signal used for the quadrature detection. Since the angular velocity of the rotational vector corresponds to the oscillation frequency (natural frequency) of the sensor oscillator, it is possible to detect the angular velocity variation of the rotational vector by detecting, for instance, the angular velocity of the rotational vector when a sensor oscillator is immersed in a solvent such as pure water, and the angular velocity of the rotational vector when supplying a liquid containing a substance to be detected into the solvent, so that the amount of adsorption of the substance to be detected adsorbed on the sensor oscillator can be obtained. It is also possible in the present invention to estimate the concentration of a substance to be detected in comparison with a calibration curve based on the angular velocity of the rotational vector by, for instance, grasping in advance the correspondence between various concentrations of a substance to be detected in a solvent and the angular velocity of a rotational vector, using the calibration curve.

Therefore, it is possible to detect the oscillation frequency of a sensor oscillator with a high degree of precision yet in an extremely short time, compared with a method of determining a frequency by counting pulses. Accordingly, the variation of an oscillation frequency of a sensor oscillator can be detected with a high degree of precision yet in an extremely short time, and it is useful as an instrument to detect a very small quantity of material including pollutant.

In addition, it is possible to generate a reversely rotational vector rotating in reverse to the above-described rotational vector at an angular velocity corresponding to the amount of variation in frequency determined by the above-described means for calculating the velocity of the rotational vector, in other words, at an angular velocity corresponding to the above-described rotational vector, and the angular velocity of the above-described rotational vector can be retarded by multiplying the above-described rotational vector by the reversely rotational vector. As a result, the angular velocity can be detected by retarding the angular velocity of the rotational vector, even when the oscillation frequency of the oscillator being used for a sensor is high, so that the measurement range of frequencies can be widened.

BEST MODE FOR CARRYING OUT THE INVENTION

Figure 1:
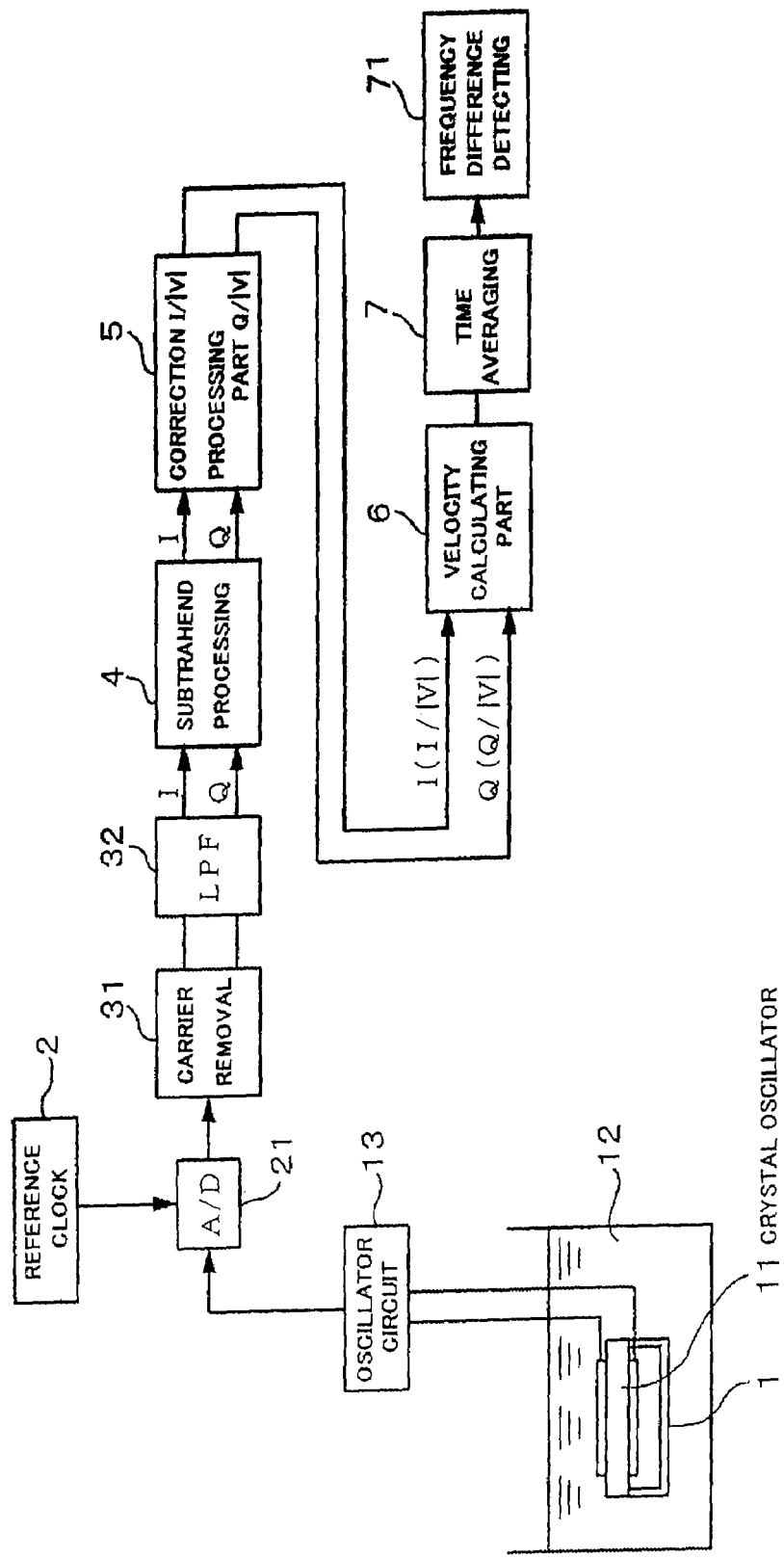
FIG. 1 is a block diagram showing the whole structure of an embodiment of a sensing instrument relating to the present invention.

FIG. 1 is a diagram showing the whole structure of an embodiment of the sensing instrument relating to the present invention. 1 is a sensor part, and this sensor part 1 is structured as a Languban typed oscillator which has a piezoelectric oscillator such as a crystal oscillator 11, which serves as a sensor oscillator, of which one surface is tightly sealed with quartz or the like and the other surface is exposed, and is, for instance, immersed in a solution 12 containing a substance to be detected. An adsorption layer to adsorb (capture) the substance to be detected, namely the adsorption layer containing an antibody to adsorb, for instance, dioxin, is formed on the surface of the above-described crystal oscillator 11, which comes in contact with the solution. 13 is an oscillator circuit to oscillate the crystal oscillator 11, outputting, for instance, a high sinusoidal wave frequency signal as a frequency signal.

2 is a reference clock generating part, outputting a clock signal which is a high frequency signal having an extremely high frequency stability for sampling the high frequency signal from the oscillator circuit 13. 21 is an A/D (analog/digital) converter, sampling the high frequency signal from the oscillator circuit 13 by a clock signal from the reference clock generating part 2 to output the sampling value in a digital value. The high frequency signal identified by the digital signal contains harmonics, in addition to a fundamental wave. In other words, when a sinusoidal wave having harmonic distortion is taken as a sample, the harmonic component is influenced by the loopback, and it is assumed that the fundamental wave frequency and the harmonic frequency are sometimes overlapped on the frequency axis in the frequency spectrum. Therefore, it is necessary to avoid such an overlapping so as to obtain a correct detection operation.

In general, when a sinusoidal wave signal of frequency f1 is sampled using a clock signal of frequency fs, the resultant frequency f2 is expressed by equation (1), in which mod (,) expresses a modulo function.

$$f2 = |\mathrm{mod}(f1+fs/2, fs) - fs/2| \quad (1)$$

Since an n-th harmonic wave frequency is expressed as n×(fundamental frequency) in terms of the fundamental frequency in the result of capturing, when it is put to be f2 and substituted into the above-described equation (1), it is possible to calculate with what frequency the harmonics can be captured. By using this calculation, it is possible to establish the frequency of the high frequency signal from the oscillator circuit 13 as fc and the sampling frequency (frequency of the clock signal) as fs so as not to overlap the frequency of the fundamental wave and the frequency of the harmonics. For instance, the fc is established to be 11 MHz, and the fs to be 12 MHz. Then, the fundamental wave of a frequency signal identified by an output signal being a digital signal from the A/D converter 21 is a sinusoidal wave of 1 MHz in this case. It should be noted that if fc/fs is taken to be 11/12, the fundamental frequency and the harmonic frequency are not overlapped with one another, but the fc/fs is not limited to this value.

A carrier removal 31 and a lowpass filter 32 are provided in this order at the post-stage of the A/D converter 21. The carrier removal 31 and the lowpass filter 32 are used to capture the rotational vector rotating at a frequency corresponding to the difference between the frequency of, for instance, 1 MHz sinusoidal wave signal identified by the digital signal from the A/D converter 21, and the frequency of a sinusoidal wave signal used for the quadrature detection.

Figure 2:
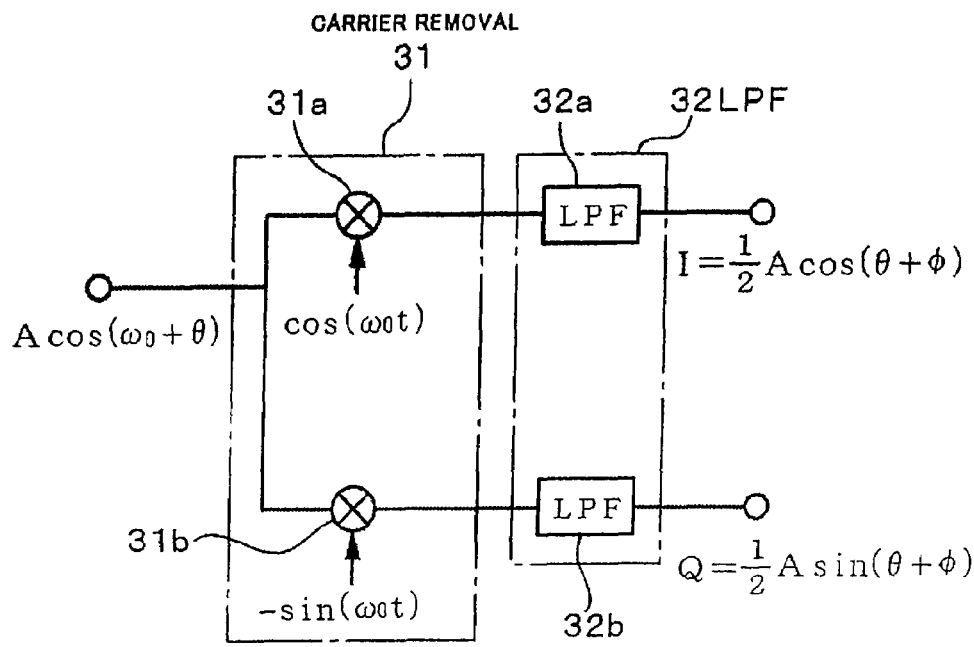
FIG. 2 is a structural diagram showing a carrier removal and a lowpass filter used in the above-described embodiment.

In order to understandably explain the operation to capture the rotational vector, the sinusoidal wave signal identified by the digital signal from the A/D converter 21 is assumed to be $A \cos(\omega_0 t + \theta)$. Whereas the carrier removal 31 is provided with a multiplication part 31a which multiplies the above-described sinusoidal wave signal by $\cos(\omega_0 t)$ and a multiplication part 31b which multiplies the above-described sinusoidal wave signal by $-\sin(\omega_0 t)$, as shown in FIG. 2. Thus, the quadrature detection is performed by such a calculation. The outputs from the multiplication part 31a and multiplication part 31b are expressed by equation (2) and equation (3), respectively.

$$A\cos(\omega_0 t+\theta)\cdot\cos(\omega_0 t) = \tfrac{1}{2}\cdot A\cdot\cos\theta + \tfrac{1}{2}\{\cos(2\omega_0 t)\cdot\cos\theta + \sin(2\omega_0 t)\cdot\sin\theta\} \quad (2)$$

$$A\cos(\omega_0 t+\theta)\cdot-\sin(\omega_0 t) = \tfrac{1}{2}\cdot A\sin\theta - \tfrac{1}{2}\{\sin(2\omega_0 t)\cdot\cos\theta + \cos(2\omega_0 t)\cdot\sin\theta\} \quad (3)$$

Accordingly, since the frequency signal at $2\omega_0$ is eliminated by allowing the output of the multiplication part 31a and the output of the multiplication part 31b to pass through lowpass filters 32a and 32b respectively, the frequency signal at $2\omega_0$ is eliminated, $\tfrac{1}{2}\cdot A\cos\theta$ and $\tfrac{1}{2}\cdot A\sin\theta$ are finally captured from the lowpass filter 32. Note that the lowpass filter 32 is described as to be structured from the lowpass filters 32a and 32b. The actual digital processing in the lowpass filter 32 calculates the moving average of a plurality of consecutive data, for instance, 6 data, for the time series data outputted from the carrier removal 31.

When the frequency of a sinusoidal wave signal expressed by A cos ($\omega 0t+\theta$) varies, A cos($\omega 0t+\theta$) becomes A cos($\omega 0t+\theta+\omega 1t$), where $\omega 1$ is assumed to be sufficiently smaller than $\omega 0$. Accordingly, ½·A cos $\theta$ becomes ½·A cos($\theta+\omega 1t$), and ½·A sin $\theta$ becomes ½·A sin ($\theta+\omega 1t$). In other words, the output obtained by the lowpass filter 32 is a signal corresponding to $\omega 1/2\pi$, that is, the frequency variation $\omega 1/2\pi$ of the sinusoidal wave signal [A cos($\omega 0t+\theta$)]. These values are a real part (I) and an imaginary part (Q), when the rotational vector rotating at a frequency difference between the sinusoidal wave signal frequency identified by the digital signal from the A/D converter 21 and frequency $\omega 0/2\pi$ of the sinusoidal wave signal frequency used for the quadrature detection.

Figure 3:
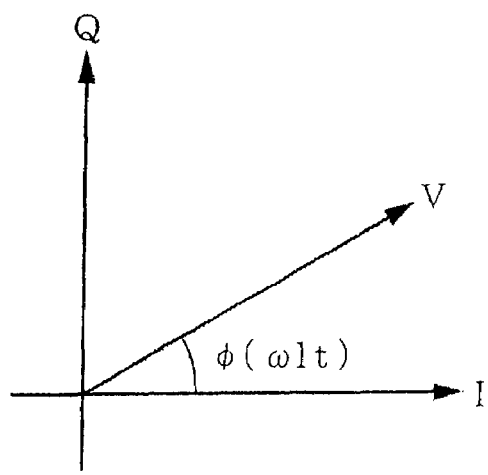
FIG. 3 is an explanatory diagram showing a rotational vector corresponding to the variation of a frequency in the frequency signal of a crystal oscillator.

FIG. 3 shows a graph showing the rotational vector, which is A in length and $\omega 1$ in angular velocity. In FIGS. 2 and 3, $\omega 1t$ is expressed as $\phi$. Accordingly, if the frequency of a frequency signal from the A/D converter 21 is $\omega 0/2\pi$ when a substance to be detected is not adsorbed by the crystal oscillator 11 for instance, $\omega 1$ is zero, and the angular velocity of the rotational vector is zero. However, when the frequency of the crystal oscillator 11 is varied by adsorption of a substance to be detected on the crystal oscillator 11, which varies the sinusoidal wave signal frequency, the rotational vector rotates at the angular velocity corresponding to the variation. When the frequency of a frequency signal from the A/D converter 21 at the time when the substance to be detected is not adsorbed on the crystal oscillator 11, is shifted from $\omega 0/2\pi$, the rotational vector rotates at the angular velocity corresponding to the shifted frequency. In any case, since the angular velocity of the rotational vector is the value corresponding to the oscillation frequency of the crystal oscillator 11, it is possible to determine the variation of the oscillation frequency caused by adsorption of a substance to be detected on the crystal oscillator 11 by seeking for respective rotational vectors when, for instance, the crystal oscillator 11 is immersed in a solvent and when the substance to be detected is added to the solvent to let the substance to be detected be adsorbed on the crystal oscillator, and by determining the difference between the angular velocities for the respective times.

Thus, the carrier removal 31 serves to perform a quadrature detection to the above-described sinusoidal wave signal, and the lowpass filter 32 serves to eliminate the high frequency component from the quadrature detection result. Accordingly, the carrier removal 31 and the lowpass filter 32 perform a quadrature detection for a frequency signal from the A/D converter 21 using a digital signal, so that they serve as a means for obtaining the real part and the imaginary part when the rotational vector rotating at an angular velocity corresponding to the frequency difference between the frequency of the frequency signal and the frequency $\omega 0/2\pi$ of the sinusoidal wave signal used to the quadrature detection is displayed in complex expression.

A subtrahend processing part 4 is provided at the post-stage of the lowpass filter 32 in FIG. 1. The subtrahend processing part 4 performs a subtrahend processing (decimation processing) to capture data, for instance, for every 120 for the time series digital signals obtained from the low pass filter 32, in other words, for a group of digital values obtained by a 12 MHz clock signal. By this subtrahend processing, the load of computer calculation can be reduced. In this embodiment, as will be described later, since the angular velocity of the rotational vector is found by determining the number of revolutions of the rotational vector during sampling intervals, the detection precision of the above-described angular velocity (detection precision of variation of the frequency) is not affected even by thinning out the digital value groups to some degree.

Figure 4:
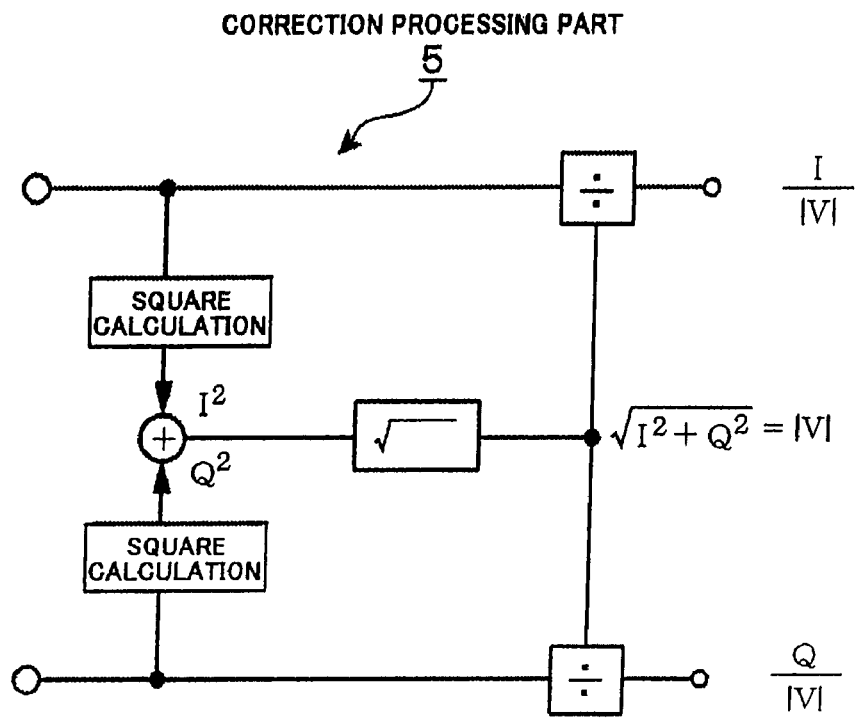
FIG. 4 is a structural diagram showing a correction processing part used in the above-described embodiment.

A correction processing part 5 is provided at the post-stage of the subtrahend processing part 4. The correction processing part 5 performs processing to determine I value and Q value per unit length of the rotational vector by dividing the I value and the Q value by scalars of the respective rotational vectors, where the I value is a real part of the above-described rotational vector and the Q value is an imaginary part, respectively passed through the lowpass filter 32 and subtrahend processed. In other words, when a symbol V is allotted to the rotational vector, the correction processing part 5 is structured in such a manner that I value and Q value are squared respectively and summed, and the square root of the summed value is calculated to find the scalar |V| of the rotational vector V so that division of the I value and the Q value by |V| can be performed, as shown in FIG. 4.

Figure 5:
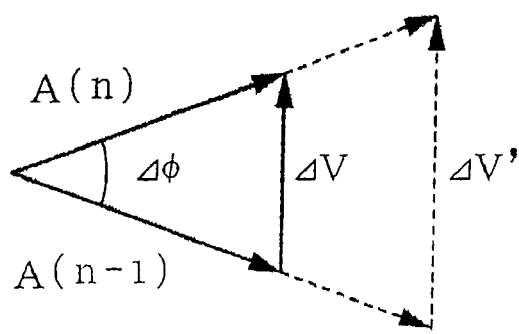
FIG. 5 is an explanatory diagram showing the manner of generating a detection error when the rotational vector is tediously extended.

The reason for correcting I value and Q value in this way is as follows. When calculating the number of rotations of the rotational vector V during the interval of the sampling in this embodiment, evaluation is made by using factors including a vector $\Delta V$ connecting the rotational vector V(n) determined by the n-th sampling to the rotational vector V(n–1) determined by the (n–1)-th sampling as shown in FIG. 5. Accordingly, when the rotational vector is, in a sense, tediously extended due to fluctuation of a wave form of the high frequency signal from the oscillator circuit 13 or the like so that $\Delta V$ becomes $\Delta V'$, the correspondence relation between $\Delta V$ and the rotational amount $\Delta\phi$ of the rotational vector is spoiled, and the reliability of the detection value of the angular velocity of the rotational vector might be compromised. Then, since I value and Q value in respective timing can be aligned as the value corresponding to a unit length of the rotational vector by performing correction processing as described before, the influence of the tedious extension of the rotational vector can be excluded.

Figure 6:
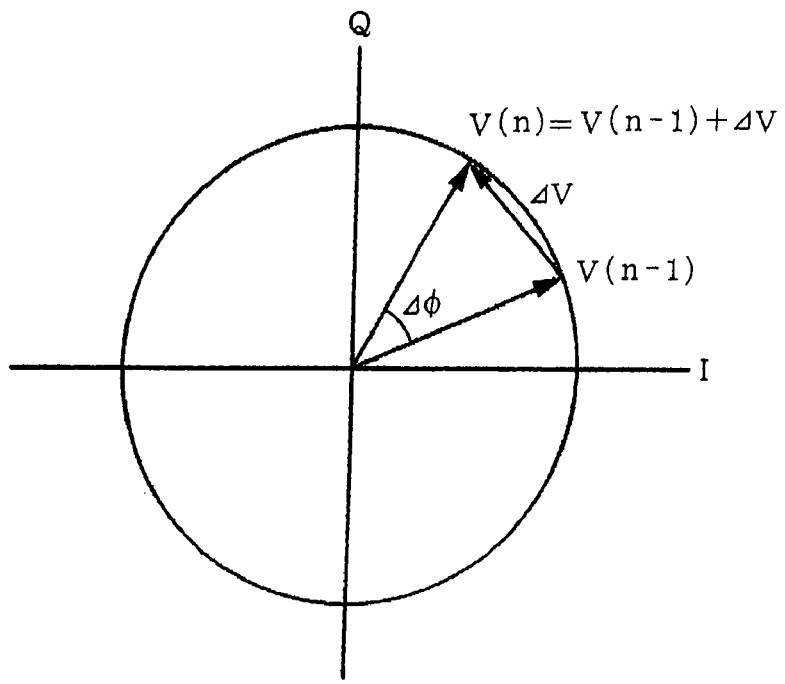
FIG. 6 is an explanatory diagram showing a phase difference between rotational vectors sampled at two successive timings.

Furthermore, as shown in FIG. 1, a velocity calculating part 6 for determining the angular velocity of the rotational vector is provided at the post-stage of the above-described correction processing part 5. The velocity calculating part 6 will be explained with reference to FIGS. 6 and 7. As shown in FIG. 6, the angle $\Delta\phi$ formed between the rotational vector V(n–1) determined by (n–1)-th sampling and the rotational vector V(n)=V(n–1)+$\Delta V$ determined by n-th sampling can be closely approximated to equation (4) when the constant is assumed to be K, and if the angular velocity (frequency) of the rotational vector is sufficiently smaller than the sampling frequency.

$$\Delta\phi = K \times \text{img}[\Delta V \cdot \text{conj } \{V(n)\}] \tag{4}$$

Where $\Delta\phi$ is the difference between the phase $\phi(n)$ of V(n) and the phase $\phi(n-1)$ of V(n–1), imag is an imaginary part, and conj $\{V(n)\}$ is a conjugate vector of V(n).

Here, if the values corresponding to the n-th sampling of I value and Q value are I(n) and Q(n) respectively, $\Delta V$ and conj $\{V(n)\}$ are expressed by equations (5) and (6) in complex notation.

$$\Delta V = \Delta I + j\Delta Q \tag{5}$$

$$\text{conj } \{V(n)\} = I(n) - jQ(n) \tag{6}$$

Where $\Delta I$ is $I(n)-I(n-1)$, and $\Delta Q$ is $Q(n)-Q(n-1)$. When the equations (5) and (6) are substituted into the equation (4) and arranged, $\Delta\phi$ can be expressed by equation (7).

$$\Delta\phi = \Delta Q \cdot I(n) - \Delta I \cdot Q(n) \qquad (7)$$

Figure 7:
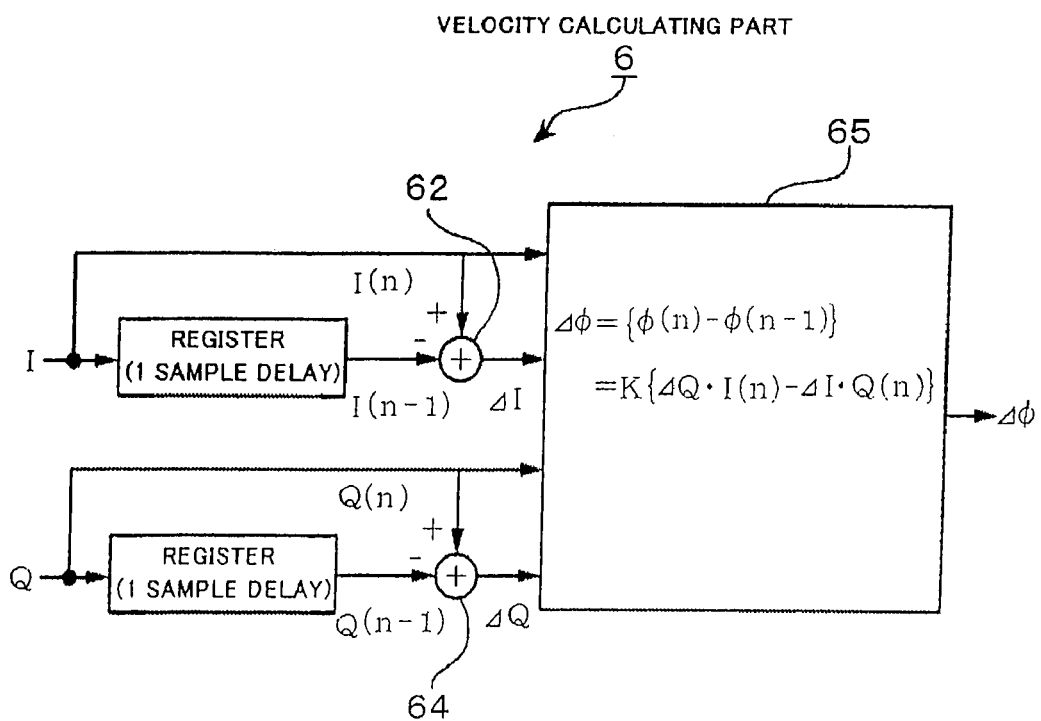
FIG. 7 is a structural diagram showing a velocity calculating part used in the above-described embodiment.

The above-described velocity calculating part 6 is to determine an approximate value of $\Delta\phi$ by calculating the equation (7), and the structure thereof is as shown in FIG. 7. When I value inputted into the velocity calculating part 6 is assumed to be $I(n)$ which is a value corresponding to the n-th sampling, $I(n-1)$ corresponding to the (n−1)-th sampling which is immediately preceding timing is held in a register 61. These are compared in a comparison circuit part 62 to take out the difference $\Delta I$ between $I(n)$ and $I(n-1)$, and $I(n)$ and $\Delta I$ are inputted to a calculating part 65. The Q value is similarly processed in a register 63 and a comparison circuit part 64, and $Q(n)$ and $\Delta Q$ are inputted into the calculating part 65. The calculating part 65 conducts the calculation of the equation (7) to determine $\Delta\phi$. For more details, the calculation result of the calculating part 65 is to evaluate as $\Delta\phi$.

Here, once the rotational vectors $V(n-1)$ and $V(n)$ are determined, it is possible to use various mathematical methods for determining or evaluating the angle $\Delta\phi$ between them. The approximate equation (4) is only an example for the method. As a mathematical expression for it, $\{V(n)+V(n-1)\}/2$, which is a vector $V0$ which connects the middle point and the original point of a line connecting the respective terminals of $V(n)$ and $V(n-1)$, is used, and this vector $V0$ may be substituted into equation (4) in place of $V(n)$. The reason why such an equation (4) can approximate is because $V0$ and $\Delta V$ can be regarded as being orthogonal, and therefore, the length of $\Delta V$ can be handled as being corresponding to the imaginary value of $\Delta V$ when $V0$ is regarded as an actual axis. An intuitively understandable method for determining $\Delta\phi$ is to find $\arg V(n)$ and $\arg V(n-1)$ and to subtract them. However, since a table associating a set of imaginary value and actual value for each vector with the phase $\phi$ for the vector is necessary in this case, it is advisable to perform calculation based on the previously described equation (4) in terms of load of computer. Note that $\arg V(n)$ is $\tan^{-1}$(imaginary value/actual value).

A time averaging processing part 7 is provided at the post-stage of the velocity calculating part 6 as shown in FIG. 1. The time averaging processing part 7 conducts time-base averaging processing for time series data of $\Delta\phi$ which are calculation results obtained in the velocity calculating part 6, for instance, taking out of the moving average of a prescribed number of data, and outputs them. The output value obtained here is inputted to a frequency difference detecting part 71. The frequency difference detecting part 71 detects the difference between the angular velocity of the rotational vector when the crystal oscillator 11 is placed in a solvent such as, for instance, pure water, which is a first environment, and the angular velocity of the rotational vector when the crystal oscillator 11 is placed in the solvent in which a substance to be detected is supplied, which is a second environment. Since an angular velocity of the rotational vector is the value corresponding to the oscillation frequency of the crystal oscillator 11, the angular velocity detection difference detected by the frequency difference detecting part 71 is a value corresponding to the variation of the oscillation frequency due to adsorption of a substance to be detected by the crystal oscillator 11, and therefore, it can be said to be a value assessing the adsorption amount of the substance to be detected. More concretely, the frequency difference detecting part 71 includes a memory to store angular velocities of respective rotational vectors, a means for reading the angular velocities of the respective rotational vectors in the memory and calculating the angular velocity differences, and so on.

The structure of the present embodiment has been explained in a blocked form as described above, but the actual calculation or data processing are conducted according to the software thereof.

The operation of the above-described embodiment will be explained next. For instance, 11 MHz frequency signal, oscillated from a crystal oscillator (oscillator circuit 13) of the sensor part 1, and including a sinusoidal wave as a fundamental wave is converted in the A/D converter 21, by, for instance, 12 MHz frequency signal, and signals including sinusoidal wave signals which are about 1 MHz fundamental waves are outputted from the A/D converter 21. Assuming that the sinusoidal wave signal is $A\cos(\omega 0t+\omega 1t+\theta)$ (where $\omega 1$ is sufficiently smaller than $\omega 0$) for convenience of the explanation here, a rotational vector rotating at an angular velocity corresponding to the variation of the frequency of the sinusoidal wave signal is captured by quadrature detection of the sinusoidal wave signal and further elimination of the lower frequency components. In other words, the real part and the imaginary part of the rotational vector are captured as I value and Q value. These I value and Q value are subtrahend processed at the subtrahend processing part 4, further divided by the scalar $|V|$ of the rotational vector V in the correction processing part 5 so that the effect of tedious extension of the rotational vector is eliminated, and the result is inputted to a frequency difference calculating part 6. It should be noted that the explanation is made by attaching the same symbol "V" to the rotational vectors before and after the correction processing to avoid complexity of the explanation.

The rotational vector V rotates at the angular velocity of the difference between a frequency of the sinusoidal signal $A\cos(\omega 0t+\omega 1t+\theta)$ and the frequency $\omega 0/2\pi$ of the sinusoidal signal used for the quadrature detection, namely, at the velocity of $\omega 1$ (refer to FIG. 3). In order to make the explanation understandable, assuming that the angular velocity corresponding to the natural frequency of the crystal oscillator 11 when the sensor 1 is, for instance, immersed in a solution for detecting the existence of a substance to be detected, and yet in the absence of the substance to be detected (at the time below the detection limit of the crystal oscillator 11) is $\omega 0$, since $\omega 1$ is zero, the rotational vector V stands still. Accordingly, $\Delta\phi$, the output of the time averaging processing part 7, is zero.

On the contrary, when a substance to be detected, for instance, dioxin exists in the above-described solution, the oscillation frequency (natural frequency) varies according to the amount of dioxin adsorbed to the crystal oscillator 11. In this case, the above-described rotational vector V starts rotation at an angular velocity corresponding to the variation of the frequency. In order to simplify the explanation, when the variation of the frequency is assumed to be 1 Hz, the rotational vector V rotates one turn in a second. Here, the present embodiment intends to detect an angular velocity of a rotational vector by finding the difference $\Delta\phi$ between the phase $\phi(n)$ of $V(n)$ and the phase $\phi(n-1)$ of $V(n-1)$ which are sampled consecutively. When the sampling interval is assumed to be $\frac{1}{100}$ second, $\Delta\phi$ is 3.6 degrees. In other words, the angular velocity of the rotational vector V is determined only within the lapse of time of the sampling interval, so that the variation of the oscillation frequency of the crystal oscillator can be determined.

Since the angular velocity corresponding to the oscillation frequency of the crystal oscillator 11 under absence of a substance to be detected quite rarely coincides with the angular velocity of the sinusoidal wave signal used for a quadrature detection, the angular velocity of the rotational vector corresponding to the oscillation frequency of the crystal oscillator 11 under absence of a substance to be detected, and the angular velocity of the rotational vector corresponding to the oscillation frequency of the crystal oscillator 11 when a substance to be detected exists are determined respectively, and the difference between these angular velocities is determined. Since the difference between the angular velocities of these rotational vectors is a value corresponding to the variation of the frequency of the crystal oscillator 11 caused by adsorption of the substance to be detected on the crystal oscillator 11, by finding the relation between the adsorption amount of a substance to be detected and the variation of the frequency in advance, it is possible to determine the adsorption amount of the substance to be detected at that time. When the relation between the concentration of a substance to be detected in a solution and the adsorption amount of the substance to be detected is determined in advance, a concentration of the substance to be detected in the solution can be found, based on the adsorption amount of the substance to be detected, in other words, the variation of the frequency of the crystal oscillator 11. Therefore, the concentration of the substance to be detected in a sample solution supplied to the solution in which the crystal oscillator 11 is immersed (symbol 12 in FIG. 1) can be determined.

Thus, according to the above embodiment, an oscillation frequency of the crystal oscillator 11 (frequency of the frequency signal from the oscillator circuit 13) is digitally processed to detect an angular velocity of the rotational vector by a phase difference corresponding to a sampling interval. As a result, it is possible to detect the variation of the oscillation frequency of the crystal oscillator 11 with a high precision and in a much shorter time compared with a conventional pulse counting method, as being supported by the later-described embodiment. Since the conventional pulse counting method counts a sinusoidal wave by changing it into a pulse, it takes as long as one second to identify, for instance, a pulse of 10 MHz with 1 Hz resolution. As clearly understood from the above explanation, the present invention is very useful as an apparatus to detect a very small amount of substances, including pollutants.

As a method of application of the present invention, it is not limited to immerse the sensor 1 into a solution, but the solution may be dripped on the surface of the crystal oscillator 11. The present invention may be used for detecting pollutants other than dioxin, for instance, such as PCB, or for detecting viruses.

Further, in the present invention, the relation between respective concentrations and angular velocities of the rotational vector is determined in advance by variously changing the concentration of a substance to be detected in a solution coming into contact with, for instance, the crystal oscillator 11, and an adsorption amount of the substance to be detected may be estimated based on the angular velocity of the rotational vector and the above-described relation, when the solution comes in contact with the crystal oscillator.

Though a state that a crystal oscillator 1 is in contact with a solvent such as pure water may be adopted as a blank value, a state that the crystal oscillator 1 is exposed in the air without being in contact with the solvent may be adopted as a blank value, so that the variation of the number of revolutions of the rotational vector when a substance to be detected is adsorbed by allowing the crystal oscillator 1 to be in contact with the solvent may be captured.

Furthermore, the present invention is not limited for detection of substances existing in a liquid, but can be applied to various fields such as detection of smell of petroleum, smoke detection at the time of fire, or detection of poison gas such as sarin gas, detection of gas in a part, detection of gas in a clean room of a semiconductor manufacturing plant, and so on.

Still further, the present invention displays the variation of a frequency itself and can use it as detection of the concentration of a substance to be detected, but the present invention may be structured as an apparatus not to detect the concentration, but to inform of only presence or absence of the substance to be detected by using a threshold value for the variation of the frequency. Since this case also use the variation of the frequency, this case is also included in the technical scope of the present invention without question.

Another embodiment of the present invention will be explained next. An object of this embodiment is to further widen the measurement range of the frequency difference in the above-described embodiment. In the previous embodiment, since the angular velocity of the rotational vector is evaluated as the length of a straight line connecting between respective terminals of V(n) and V(n−1) as shown in FIG. 6, if the phase difference of these vectors is large, the measurement error becomes large. Therefore, in this embodiment, a reversely rotational vector reversely rotating at an angular velocity corresponding to the angular velocity of the rotational vector is prepared, and the rotational vector and the reversely rotational vector are multiplied together, so that the angular velocity of the rotational vector is reduced. Thus, the phase difference between V(n) and V(n−1), namely, the angular velocity of the rotational vector is detected at a high precision no matter how fast or slow the rotational vector may be, so that it intends to widen the measurement range of the variation of frequency (frequency difference) at the time of supplying a sample solution to a sensor.

Figure 8:
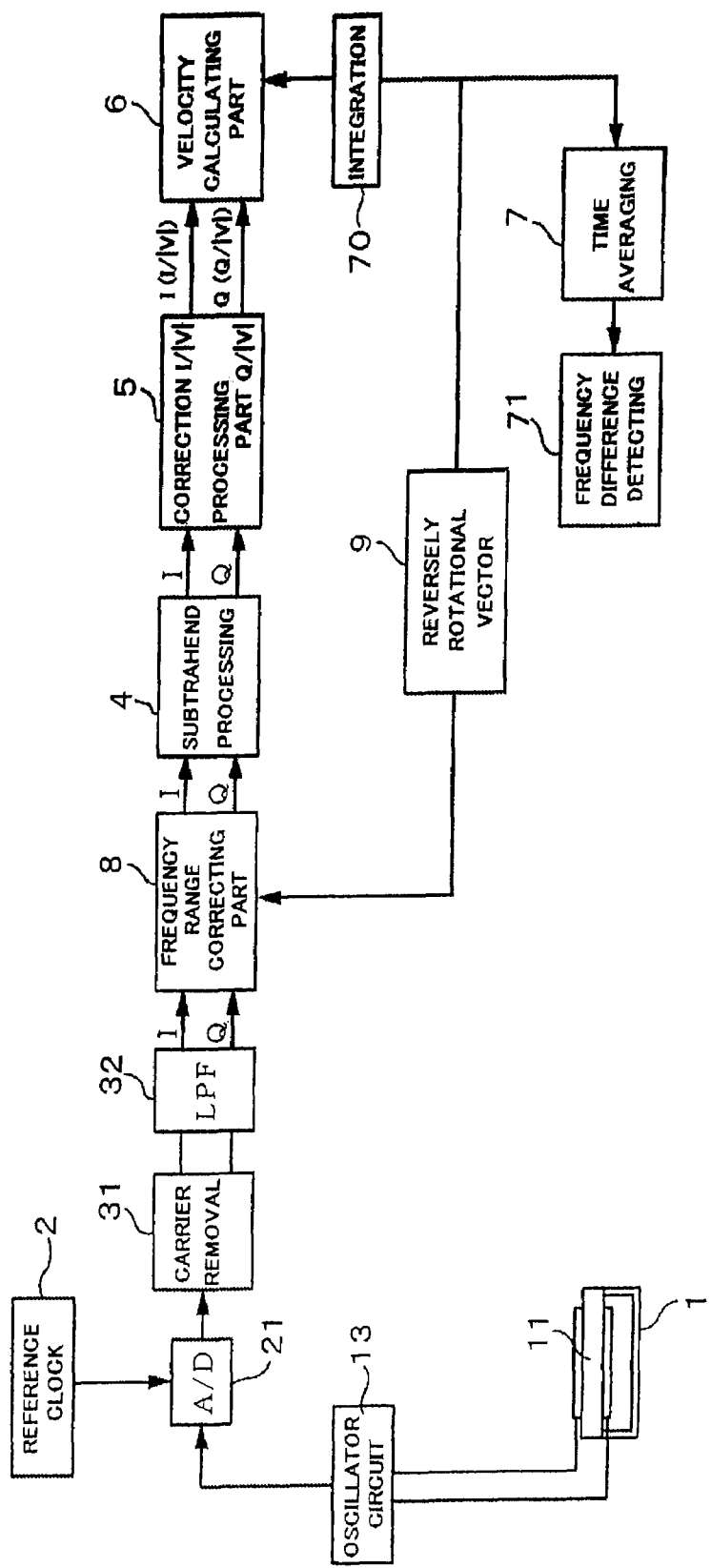
FIG. 8 is a block diagram showing the whole structure in another embodiment of the present invention.

FIG. 8 shows the entire structure of this embodiment, in which an integrator 70 is provided between the output terminal of the frequency difference calculating part 6 and the time averaging processing part 7. Whereas, a frequency range correcting part 8 is provided between the lowpass filter 32 and the subtrahend processing part 4, and a reversely rotational vector generating part 9 generating a reversely rotational vector rotating in the opposite direction to the previously-described rotational vector V is provided in response to the output of the integrator 70. A reversely rotational vector generated here and a rotational vector identified by time series data outputted from the lowpass filter 32 are multiplied in the frequency range correcting part 8.

Figure 9:
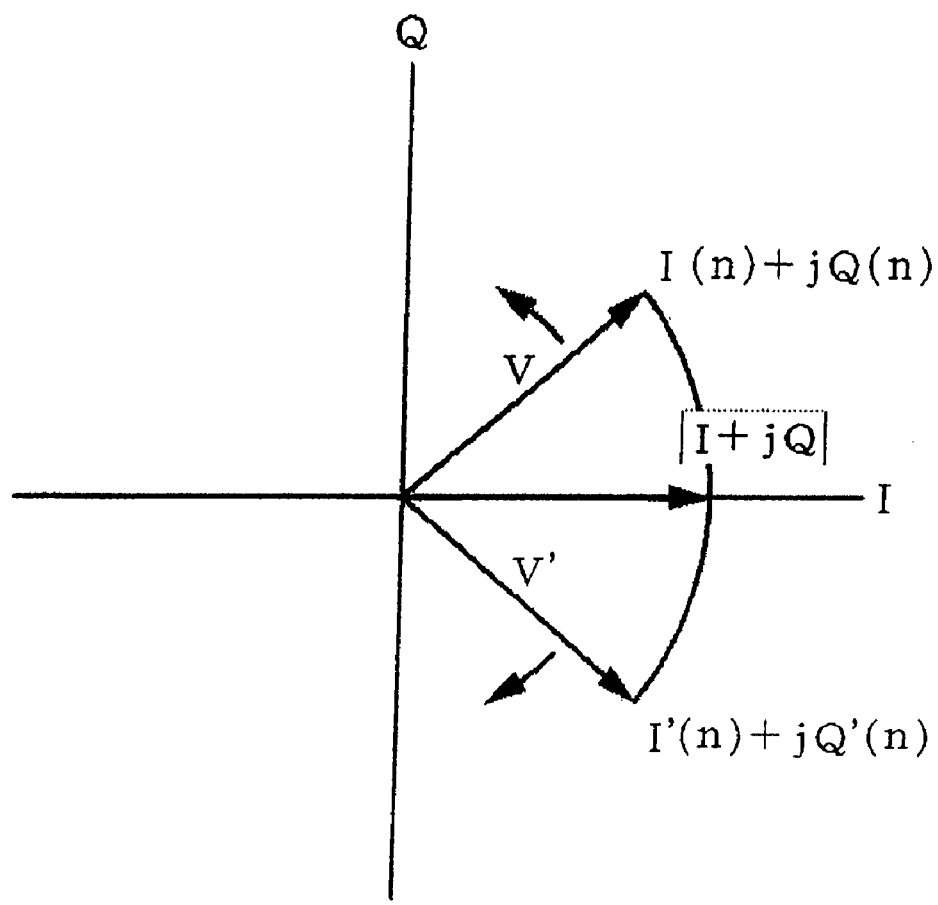
FIG. 9 is an explanatory diagram showing the manner of multiplying the rotational vector and the reversely rotational vector in the above further embodiment of the present invention.

Now, a frequency difference (frequency variation) is assumed to be, for instance, 500 Hz, and as to the rotational vector corresponding to the frequency difference 500 Hz, a sampling value at a certain timing, for instance, at n-th time, is assumed to be I(n)+jQ(n) as shown in FIG. 9. When this vector is put back to a position along an actual axis, it is advisable to prepare a reversely rotational vector V' rotating in the opposite direction to the above-described rotational vector V at an angular velocity corresponding to the frequency difference 500 Hz, and to multiply the vector by the reversely rotational vector V'. A vector I+jQ formed by putting back of the rotational vector V by the reversely rotational vector V' becomes $\{I(n)+jQ(n)\} \times \{I'(n)+jQ'(n)\}$. Equation (8) is obtained by rearranging this equation, and the frequency range correcting part 8 conducts calculation of this equation.

$$I+jQ=\{I(n) \cdot I'(n)-Q(n) \cdot Q'(n)\}+j\{I(n) \cdot Q'(n)+I'(n) \cdot Q(n)\} \quad (8)$$

Figure 10:
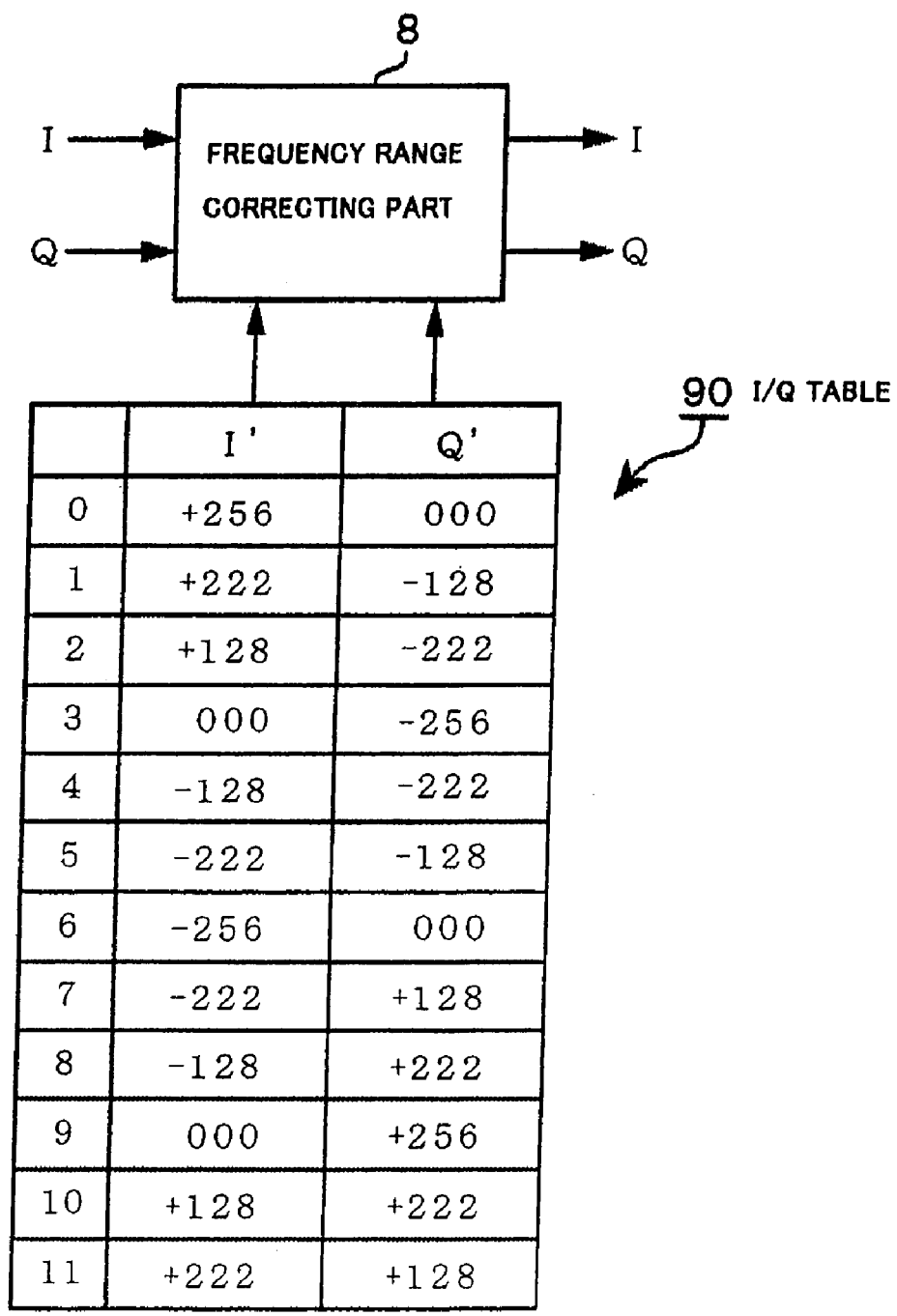
FIG. 10 is an explanatory diagram showing a data table to generate the reversely rotational vector in the above further embodiment of the present invention.

To generate the reversely rotational vector V' is, practically, to make values of cos φ and sin φ come into existence assuming that values of the real part and the imaginary part of the vector, namely, the phase of the reversely rotational vector V' is φ, so that a vector on the complex plane reversely rotates. FIG. 10 shows an I/Q table 90 in which sets of cos φ and sin φ of the vector are arranged in sequence along the rotational direction of the vector. The reversely rotational vector generating part 9 includes the above-described I/Q table 90 in this example, reads the addresses in the I/Q table 90 using an increment number or a decrement number according to the output of the integrator 70, and outputs them to the frequency range correcting part 8. For instance, the address is read one by one from "0" to "11" at the clock readout timing. On returning to "0" again, the vector makes one rotation clockwise on the complex plane in 12 clocks, and when the addresses are read at every other address by setting the increment number to 2, the angular velocity of the vector is doubled. Accordingly, it is possible to generate the reversely rotational vector reversely rotating at an angular velocity according to the frequency difference Δφ (angular velocity according to the angular velocity of the rotational vector V) calculated at the previously described frequency difference calculating part 6 (refer to FIG. 8) by determining an increment number according to the magnitude of the integrator 70.

As described previously, since the rotational vector V rotates at the angular velocity ω1 (refer to FIG. 3), when the sinusoidal wave signal $A\cos(\omega 0 t+\theta)$ deviates to $A\cos(\omega 0 t+\theta+\omega 1 t)$, the direction of rotation as for whether it rotates clockwise or anticlockwise is determined depending on the value ω1. Accordingly, the direction of the reversely rotational vector V' is determined according to the direction of the rotational vector V, and the output of the integrator 70 becomes a positive value or a negative value according to the direction. As for readout of the address in the I/Q table 90, when the output of the integrator 70 is a positive value, the readout is conducted with an increment number according to the positive value, and when the output of the integrator 70 is a negative value, the readout value is conducted with a decrement number according to the negative value. In other words, the I/C table 90 is in the relation of cos and sin, and the correction direction of the rotational vector V is controlled by incrementing or decrementing the address of the I/Q table 90 in an address controlling part 103. Note that the I/Q table in FIG. 10 is diagrammatically prepared to make the understanding of the present invention easy, and is not a preferable example of preparation for an actual table.

Figure 11:
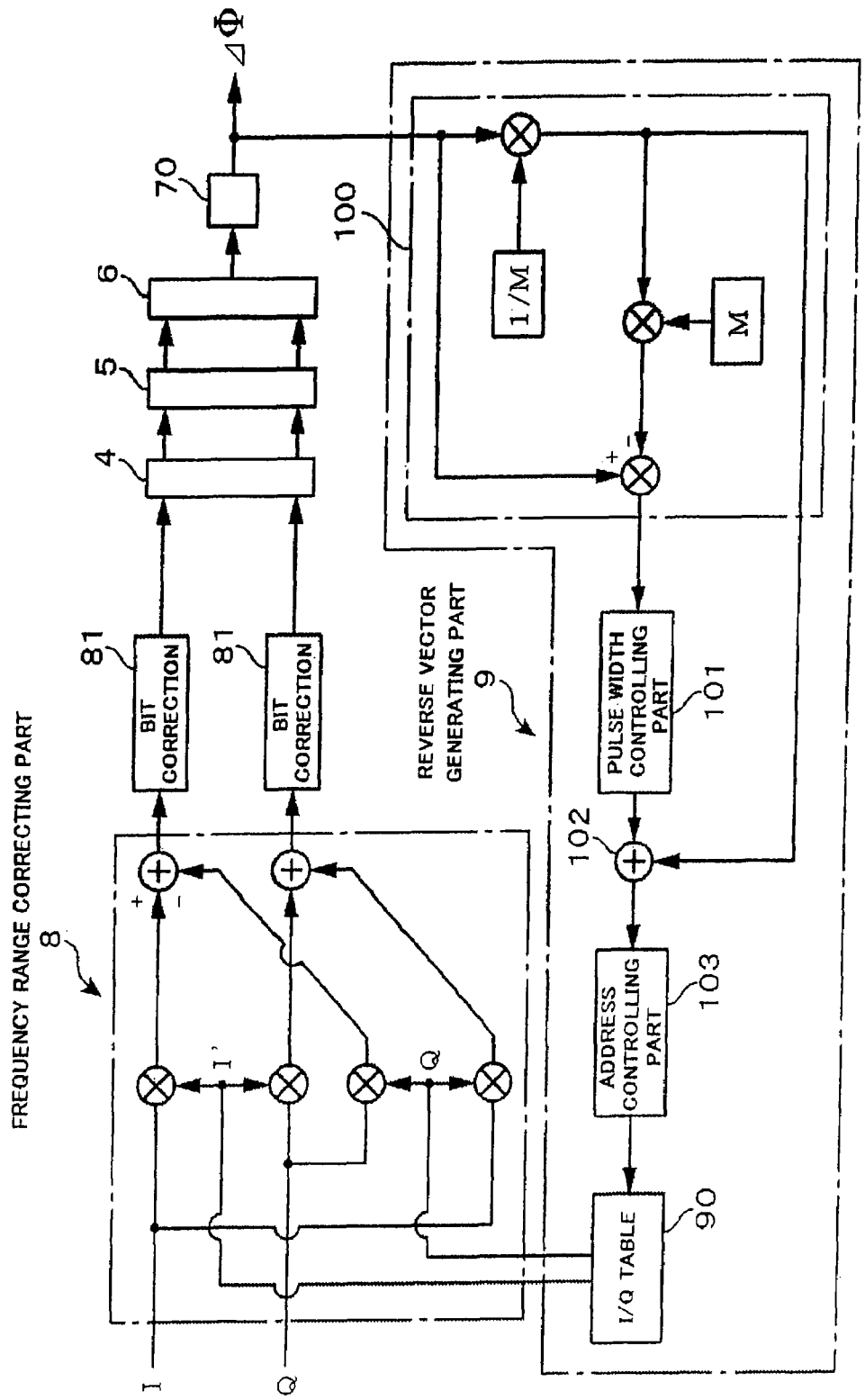
FIG. 11 is a block diagram showing the structure of the main part in detail in the above further embodiment.
Figure 12:
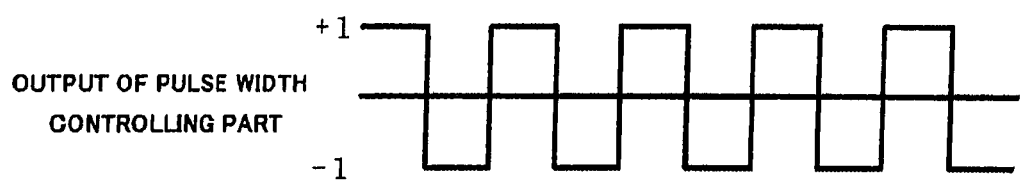
FIGS. 12A, 12B, 12C and 12D are timing charts showing one function in the above further embodiment.
Figure 12:
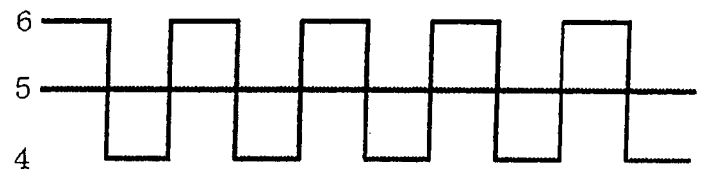
Figure 12:
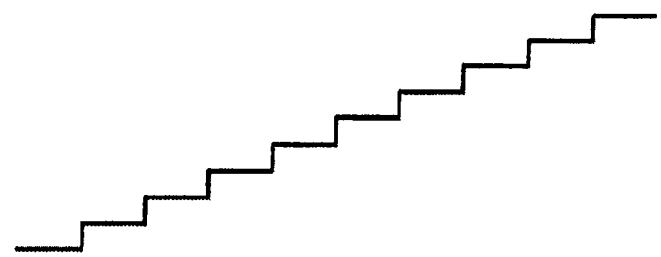

A preferable example of the reversely rotational vector generating part 9 is shown in FIG. 11. The reversely rotational vector generating part 9 is provided with a bit dividing part 100 which divides an output value from the integrator 70 into a higher rank bit value and a lower rank bit value in this example. For instance, when an output value of the integrator has 16 bits, it is outputted by dividing it into a higher 8-bit value and a lower 8-bit value. In this example, the higher 8-bit value (decimal converted value) is prepared by multiplying a higher 8-bit BCD code (binary-coded decimal) value among the output values from the integrator 70 expressed in 16 bits by I/M (where M is minus 8th power of 10), and thus-obtained value is multiplied by M to get the value restored to the original higher 8-bit BCD code value. Then, the lower 8-bit value (decimal converted value) is prepared by subtracting the above value from the 16-bit BCD code value which is previously described output value. It should be noted that the method for dividing an output value from the integrator 70 into a higher rank bit value and a lower rank bit value is not limited to this method, and may simply take out a higher rank bit value and a lower rank bit value.

A pulse width controlling part 101 is provided on the output side of the lower rank bit (on the output terminal side outputting a lower 8-bit value in this example) of the bit dividing part 100, and an adder 102 is provided at the post-stage of the pulse width controlling part 101, so that a pulse train outputted after pulse width controlling according to a lower rank bit value, and a higher rank bit value are added by the adder 102. An address controlling part 103 is provided on the post-stage side of the adder 102, and the address controlling part 103 is structured to integrate a value obtained by the adder 102, and control readout of the address in the I/Q table 90 according to the integrated value, in other words, to control the increment number or the decrement number of the address.

The operation of this embodiment will be explained next. When the frequency of the crystal oscillator 11 is deviated from the state that a substance to be detected is not adsorbed by adsorption of the substance to be detected on the crystal oscillator 11 first, the rotational vector V rotates at the angular velocity corresponding to the frequency difference which is the variation of the frequency. Then, a signal at a level of a higher rank bit level, for instance, a higher 8-bit value, in the output value of the integrator 70 corresponding to the angular velocity of the rotational vector V is inputted to the adder 102. Whereas, a lower rank bit value, for instance, a lower 8-bit value, in the output value of the integrator 70 is inputted to the pulse width controlling part 101. A pulse width calculation is conducted by sampling signals generated at every pulse numbers previously established for the clock pulse of computer in the pulse width controlling part 101, and the pulse train at the duty ratio corresponding to an input value is outputted.

The pulse train is a combination of a +1 level pulse generated in one clock and a −1 level pulse generated in one clock. Assuming that pulse width calculation is conducted every 20 clocks, and the duty ratio corresponding to the input value of the pulse width controlling part 101 is 50%, the +1 level pulse and the −1 level pulse are outputted 10 pulses each alternately as shown in FIGS. 12A, 12B, 12C and 12D. When a level corresponding to, for instance, a higher 8-bit value is assumed to be "5", "6" and "4" are outputted alternately from the adder 102 during a period from generation of a sampling signal to generation of the next sampling signal, the address controlling part 103 integrates these output values, and the integrated values thereof become addresses of the I/Q table 90. That is, since the increased portion of the integrated value is alternate repeat of "6" and "4" in this case, the increment number of the address is alternate repeat of "6" and "4", and as a result, the address is accessed with the increment number of average "5", which is the level corresponding to the higher 8-bit value, so that a real part and an imaginary part of the reversely rotational vector V', which are described in the address, are read out. In short, the reversely rotational vector V' rotating at an angular velocity corresponding to this "5" is generated. Note that the I/Q table 90 in FIG. 10 is prepared to make the understanding easy, and is not matched with the movement in this case. Thus, calculation according to previously-described equation (8) is conducted for the respective values of the real part and the imaginary part read out from the I/Q table 90 in the frequency range correcting part 8, so that the rotational vector V is multiplied by the reversely rotational vector V'. Note that 81 is a bit processing part which conducts a rounding-off processing of a lower rank bit to reduce the number of calculation bits after the frequency difference calculating part 6.

Since the reversely rotating vector generating part 9 shown in FIG. 11 forms a phase lock loop (PLL), when a signal value inputted to the frequency range correcting part 8 from the lowpass filter 32 side is stabilized, the angular velocity of the rotational vector V and the angular velocity of the reversely rotational vector V' are immediately locked to be in a stable state, and the respective signals are as shown in FIG. 2. In other words, the angular velocity of the rotational vector V is reduced by the reversely rotational vector V' so that the rotational vector V is stabilized, but since this angular velocity corresponds to the angular velocity at the time when the rotational velocity V is not multiplied by the reversely rotational vector V', the angular velocity of the rotational vector V locked by the PLL corresponds to the frequency difference of a crystal oscillator, and the measurement range is widened as a result. In short, it is possible to determine the angular velocity, namely, to measure the variation of the frequency, even when the variation of the frequency is large resulting in large angular velocity of the rotational vector.

Figure 13:
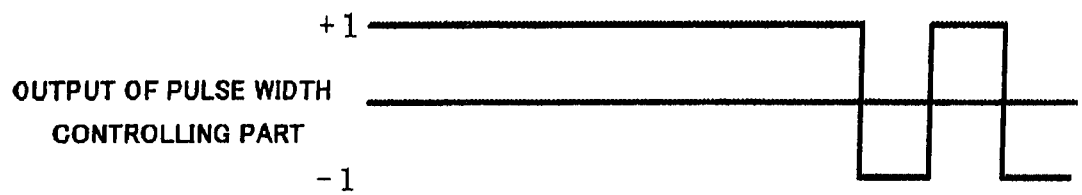
FIGS. 13A, 13B, 13C and 13D are timing charts showing one function in the above further embodiment.
Figure 13:
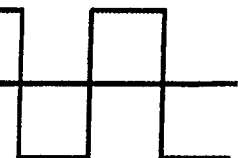
Figure 13:
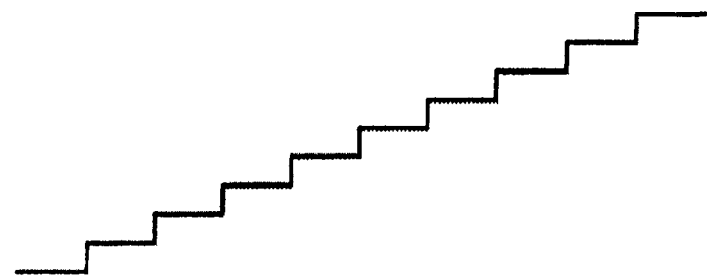

When the duty ratio corresponding to an input value of the pulse width controlling part 101 is more than 50%, pulses at a +1 level last by the numbers corresponding to a portion exceeding 50% as shown in FIG. 13, and the pulse at +1 level and the pulse at −1 level are generated alternately thereafter. Accordingly, since "6" lasts at first in the increment of the integrated value of this pulse train, the increment number of the address is continuously "6", then "6" and "4" are alternately repeated. Accordingly, the average value of the angular velocity of the reversely rotational vector V' during the interval from the sampling of an input value of the pulse width controlling part 101 to the next sampling is between an angular velocity corresponding to "5" and an angular velocity corresponding to "6", and is a magnitude according to the above-described duty ratio. In other words, this angular velocity corresponds to a value of "5" plus the fractional portion of "5", which means the interval between "5" and "6" is interpolated according to the inputted value of the pulse width controlling part 101 (the lower rank bit value in the output of the integrator 70). It should be noted that in this example, the timing of pulse width calculation is 20 clocks each, but the clock number may be, for instance, the bit number of the lower rank bit, that is 8 in this example, and the pulse width calculation may be conducted for every 8 clocks.

Thus, when adopting a method of determining the increment number for the address of the I/Q table 90 to be in accordance with the output value of the integrator 70 output without providing the bit dividing part 100 and the pulse width controlling part 101, the I/Q table 90 is required to be a number according to the required precision (detecting and resolution for frequency difference), and the number becomes larger than in the case of using a pulse width control. On the contrary, when it is structured as in the present embodiment, the memory capacity of the I/Q table 90 can be reduced by the amount to be complemented by the pulse width control.

Figure 14:
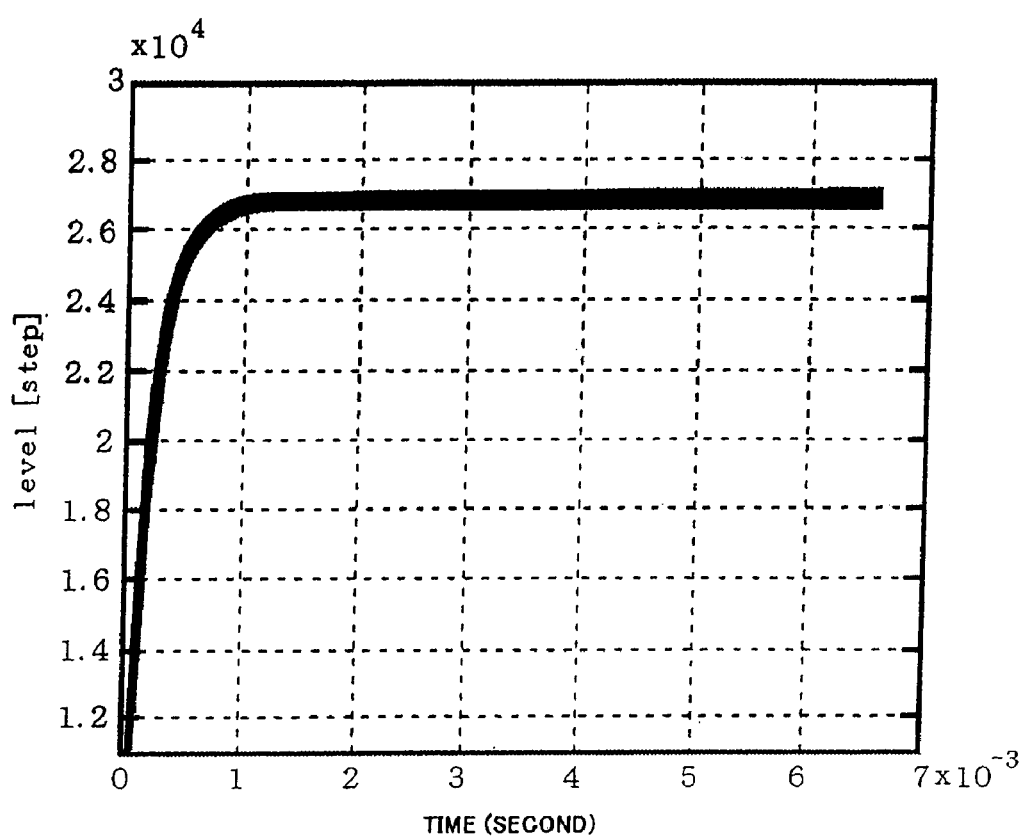
FIG. 14 is a characteristic diagram showing an example of the input value of a pulse width circuit part used in the above further embodiment.
Figure 15:
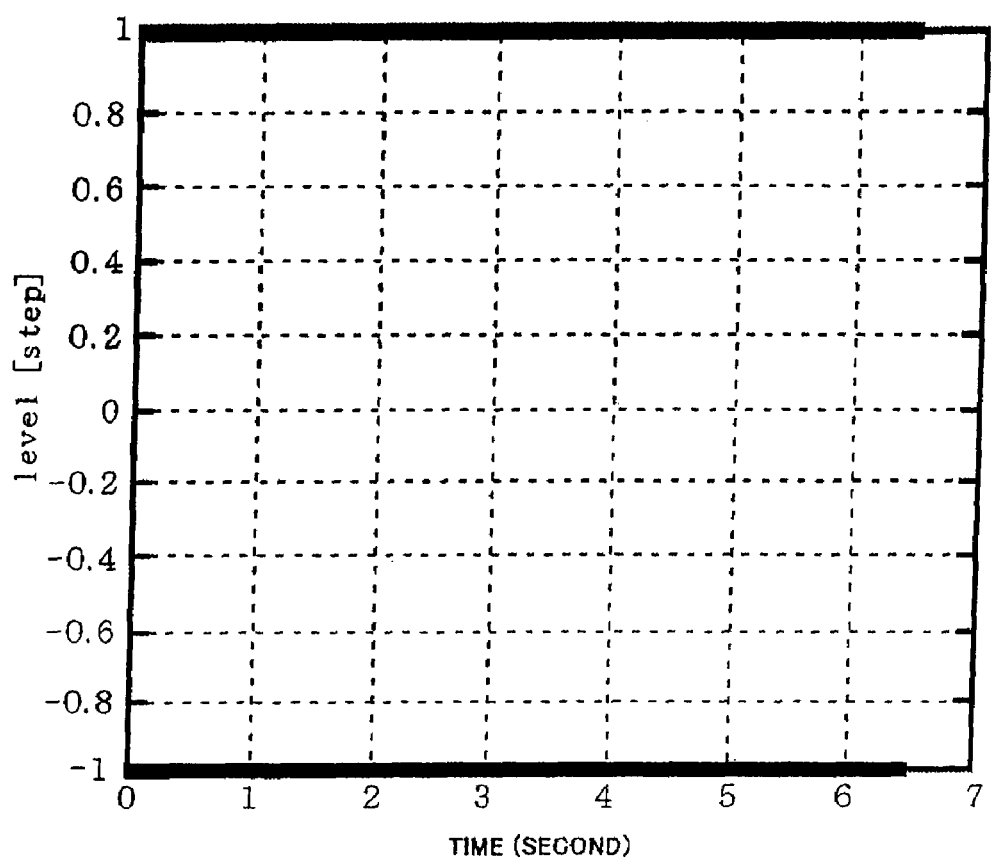
FIG. 15 is a characteristic diagram showing an example of the output value of the above-described pulse width circuit part.
Figure 16:
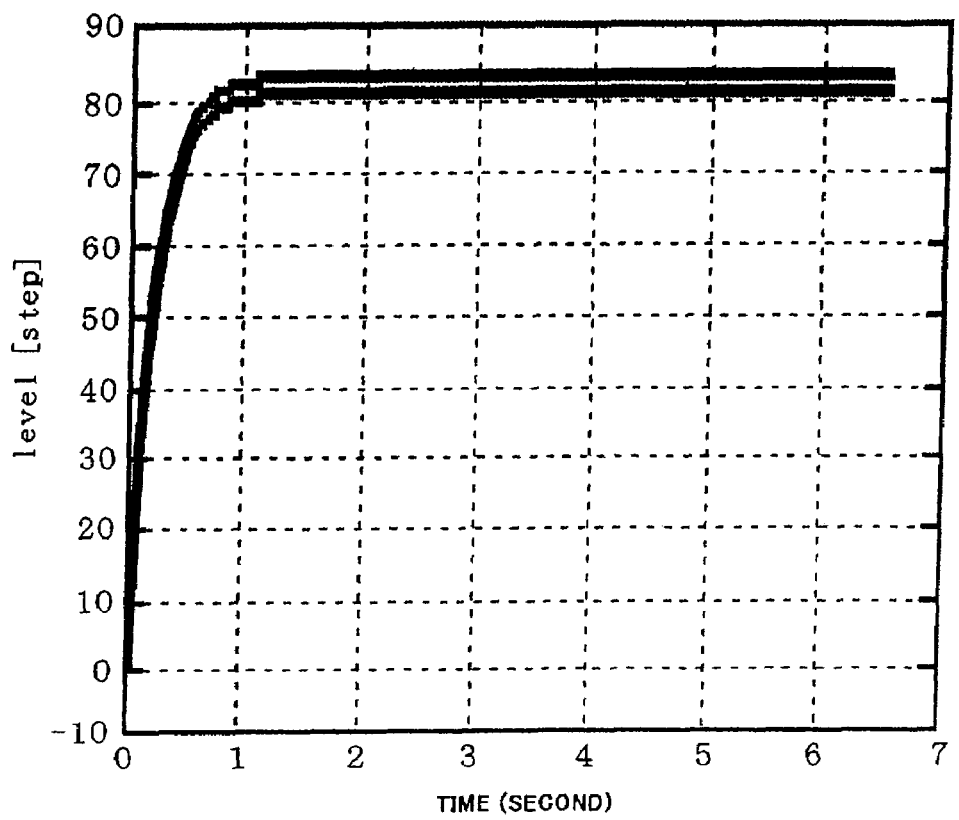
FIG. 16 is a characteristic diagram showing an example of the output value of an adder used in the above further embodiment.

The case that the frequency difference of a crystal oscillator is 500 Hz is taken as an example of the case that the output value of the integrator 70 does not appear in a higher rank bit, and the variation of the input level and the output level of the pulse width controlling part 101 through simulation is studied. The results of the study are shown in FIG. 14 and FIG. 15 respectively. As shown in FIG. 14, the input level of the pulse width controlling part 101 is stable at nearly 1 msec, which shows that the angular velocity of the rotational vector V is locked instantaneously by the PPL including the reversely rotational vector generating part 9. The outputs of the pulse width controlling part 101 are actually level signals between +1 and −1, and these values are inputted to the address controlling part 103, but the outputs are drawn in a straight line at +1 and −1 because of the resolution of drawing. As for the case that the output value of the integrator 70 appears in a higher rank bit, taking the case of the frequency difference of a crystal oscillator being 10000 Hz as the example, the output levels of the adder 102 are shown in FIG. 16. In this example, the outputs of the adder 102 are almost stable at "81".

According to the other embodiments described above, the following further effect can be found in addition to the effect of the previous embodiment. Since the rotational vector V corresponding to the variation of frequency (natural frequency) of a crystal oscillator is multiplied by the reversely rotational vector V', so that the angular velocity of the rotational vector V is reduced, as shown in FIG. 6, even when an angular velocity of the rotational vector V is evaluated as the length of a straight line connecting between a vector at a certain timing and a vector at the next timing, the angular velocity of the rotational vector V can be determined with a high precision, and as a result, an angular velocity can be determined with a high precision no matter how high or low the angular velocity of the rotational vector V may be. Therefore it is possible to measure the variation of the natural frequency of a crystal oscillator from a large value to a small value of the variation, which results in widening of the measurement range. Furthermore, the angular velocity of the rotational vector V to be fed back is classified into a higher rank bit value and a lower rank bit value, and as the lower rank bit values, the data values of the I/Q table 90 are interpolated using pulse width control. Accordingly, the size of the I/Q table 90 can be made small as described previously in detail, so that the circuit scale can be reduced.

Figure 17:
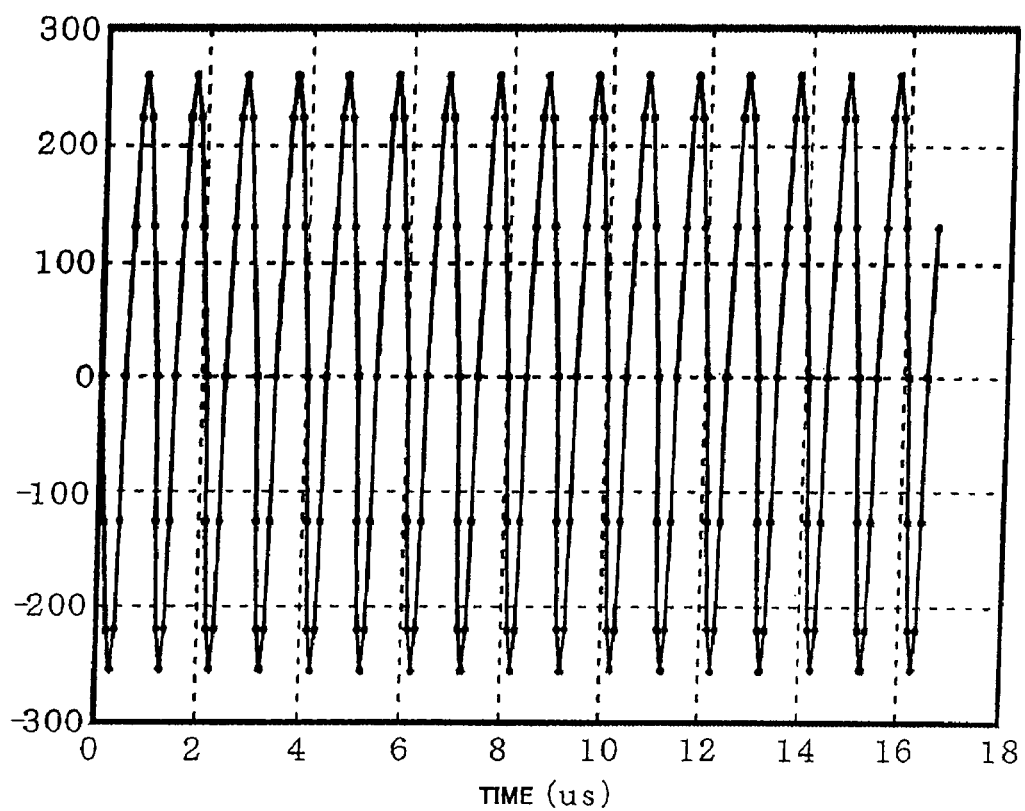
FIG. 17 is an explanatory diagram showing the manner of sampling a frequency signal from the oscillator circuit of the crystal oscillator and converting it to the digital value in a concrete example of the present invention.
Figure 18:
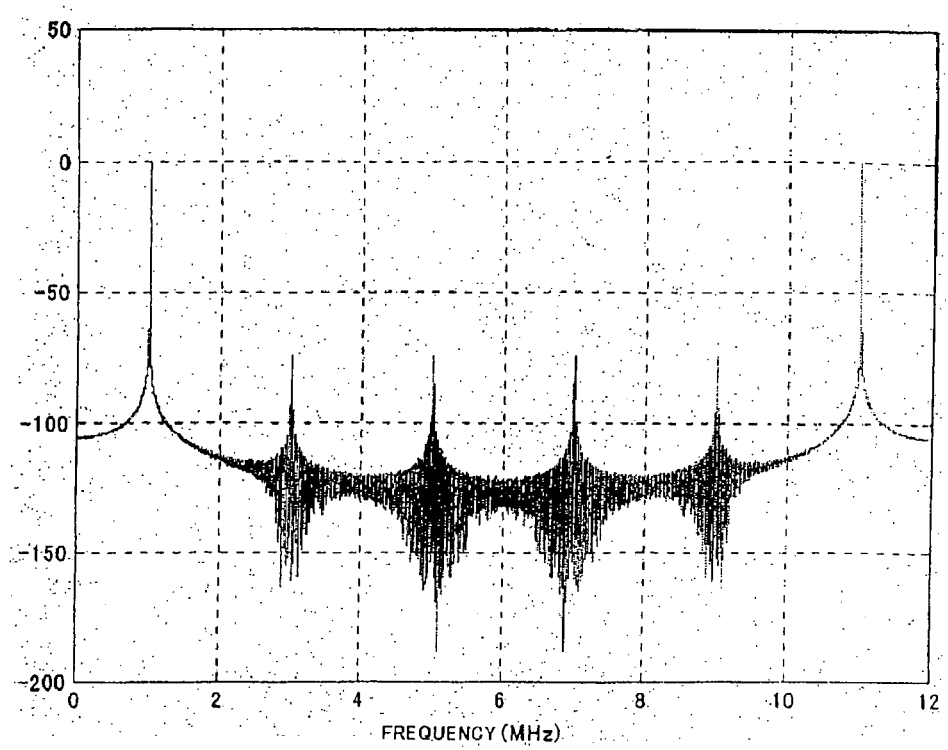
FIG. 18 is a characteristic diagram showing the result of verification for the frequency spectrum of the output signal obtained in FIG. 8.

As an experiment to verify the instrument of the present invention, the frequency fc of the frequency signal from the oscillator circuit 13 is assumed to be 1 MHz, the frequency fs of the reference clock signal is assumed to be 12 MHz, and actual data processing is conducted by a computer. The frequency of a high frequency signal (sinusoidal wave signal) for the test used as the frequency signal from the oscillator circuit 13 is slightly deviated from 1 MHz. FIG. 17 is a view showing the manner of sampling a high frequency signal for the test with a reference clock signal to determine the digital value. When the frequency spectrum is studied for the signal identified by thus obtained digital value, it is as shown in FIG. 18. Accordingly, the high frequency signal which is a 1 MHz sinusoidal wave signal as the fundamental is taken out from the A/D converter 21 here.

Figure 19:
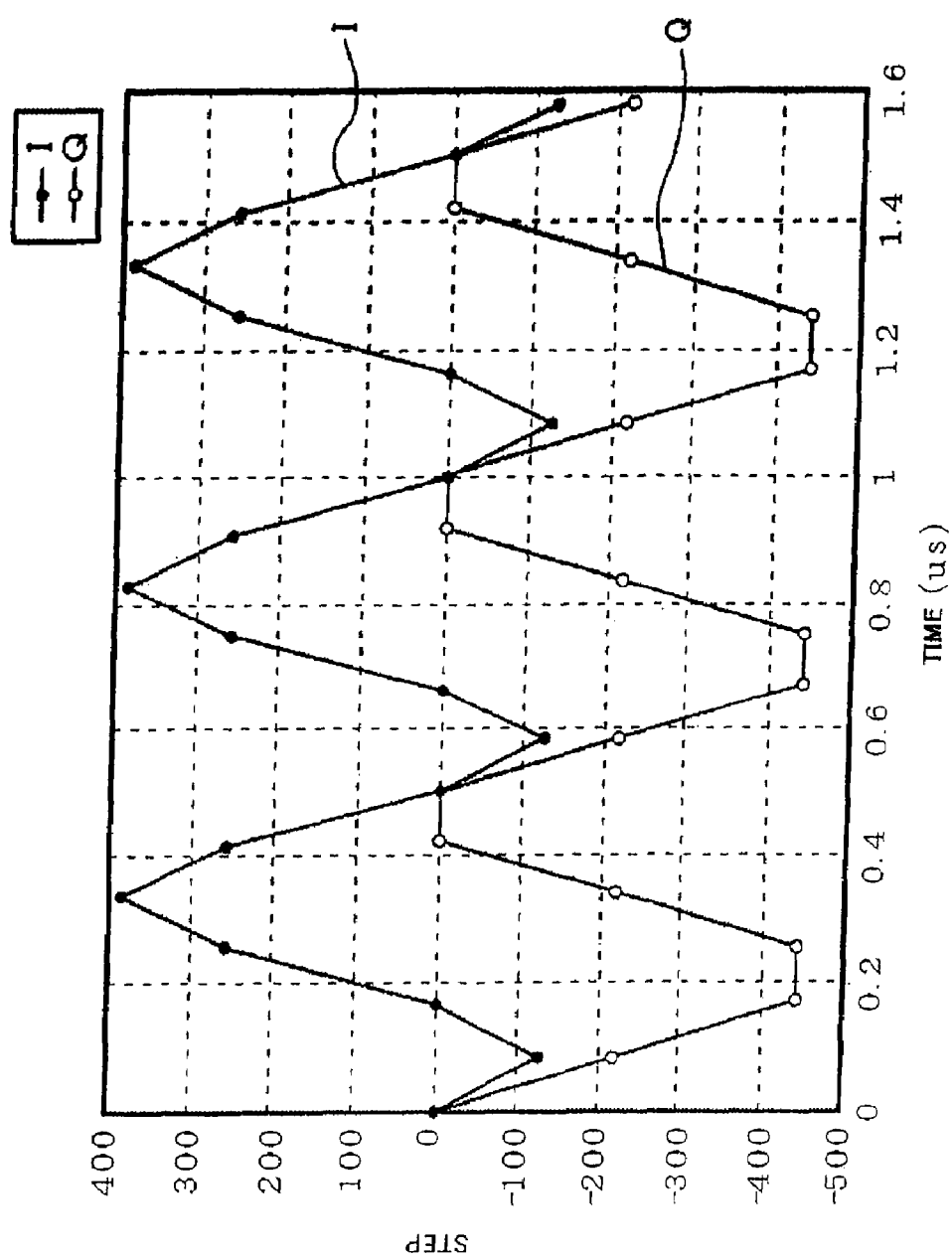
FIG. 19 is a characteristic diagram showing I values and Q values obtained in the carrier removal in the above described embodiment.
Figure 20:
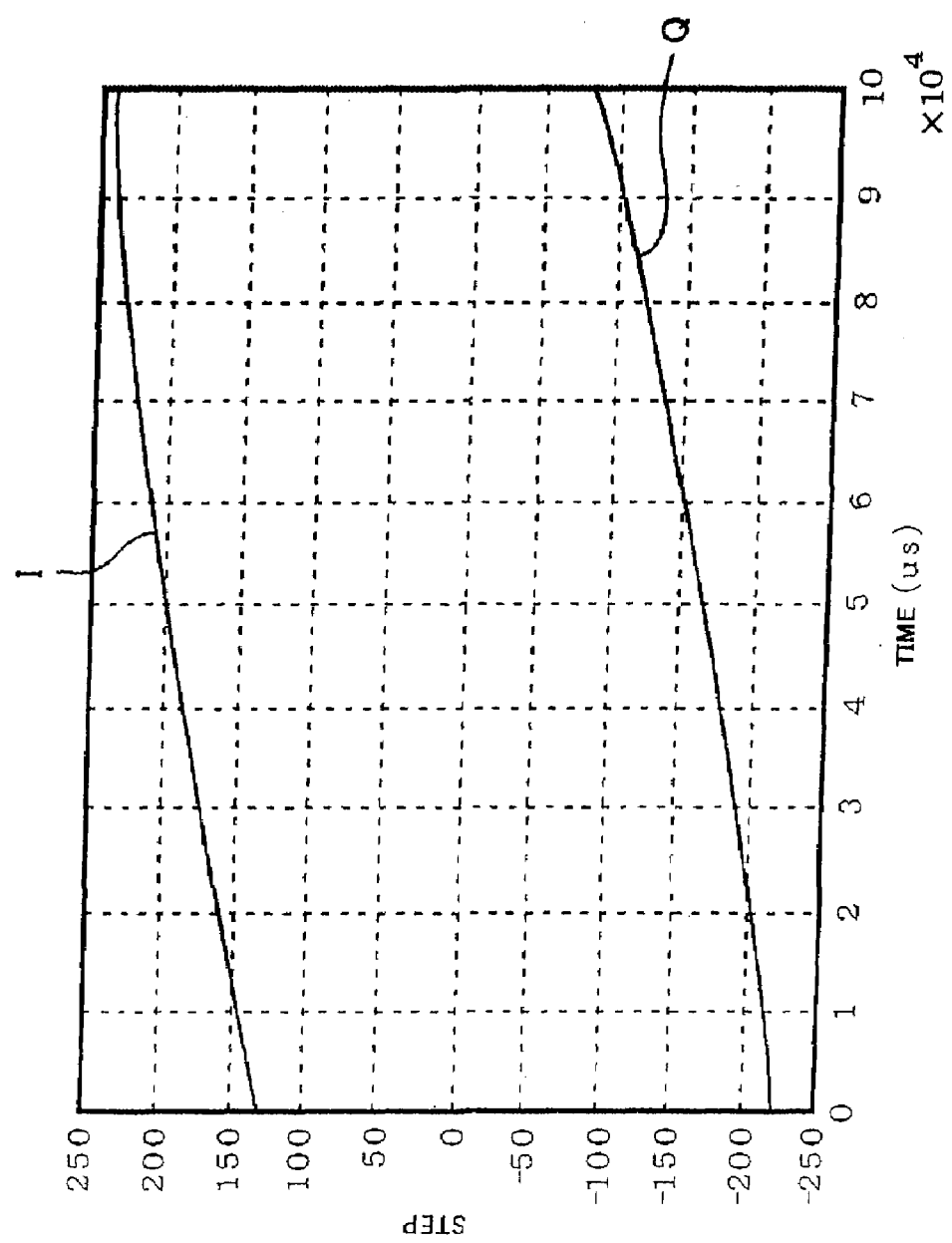
FIG. 20 is a characteristic diagram showing I values and Q values obtained in the lowpass filter in the above described embodiment.
Figure 21:
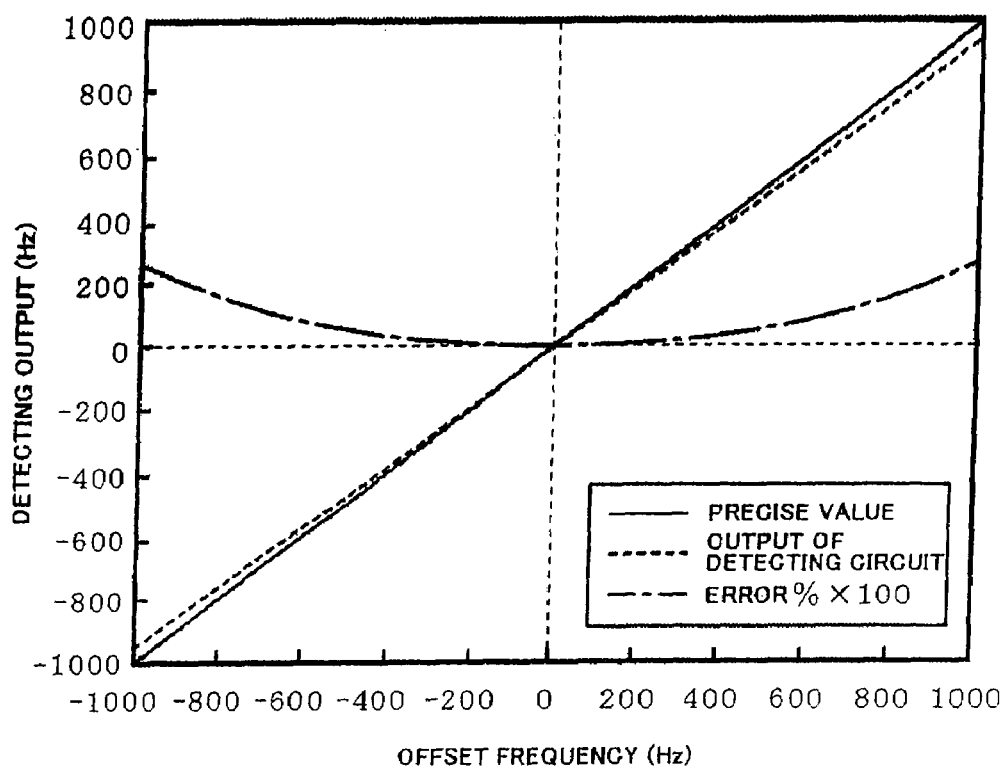
FIG. 21 is a characteristic diagram showing the relation between offset frequencies and detected outputs in the above-described embodiment.
Figure 22:
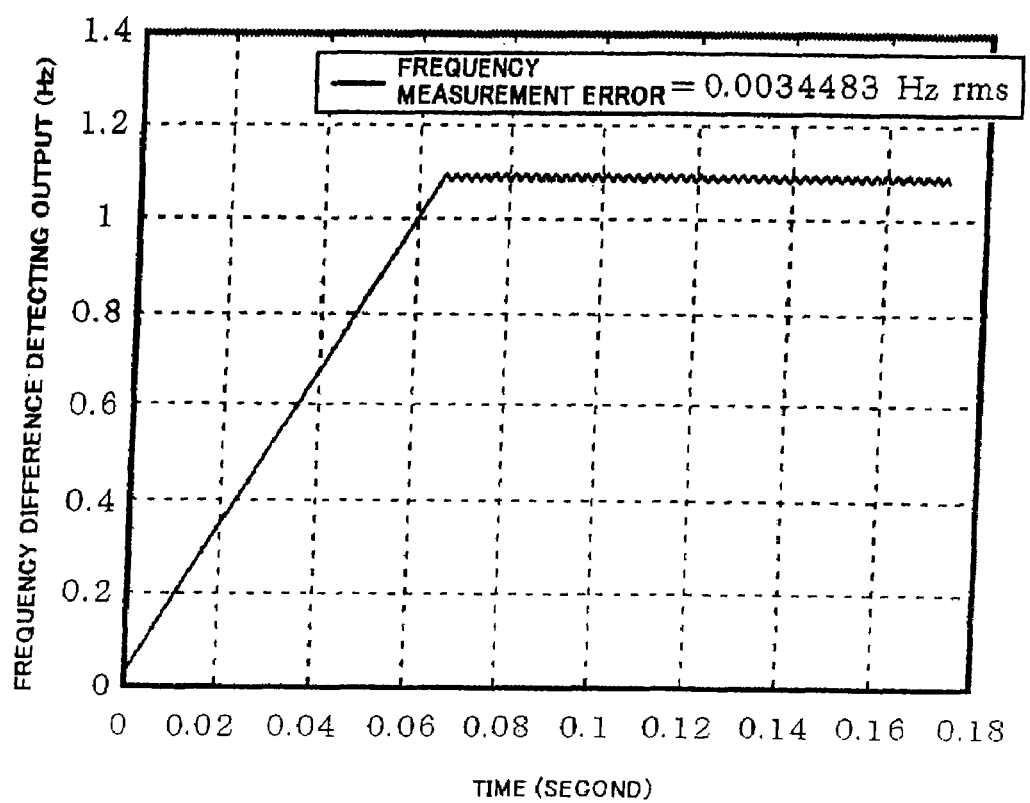
FIG. 22 is a characteristic diagram showing the manner on leading edge of the detected value of the amount of frequency variation in the above-described embodiment.

FIG. 19 shows I values and Q values outputted from the carrier removal 31, and FIG. 20 shows I values and Q values obtained from the lowpass filter 32. Since the frequency is varied for the high frequency signal for the test in this example, the output values from the lowpass filter 32 are increasing. FIG. 21 shows the relation between the offset frequency (the amount of variation in frequency) and the detected output in this embodiment. As the offset frequency increases, errors thereof becomes significant, but in a region where the offset frequencies are small, the correspondent relation between both is extremely favorable, and the possibility to detect the amount of variation in frequency with high reliability can be understood. FIG. 22 shows the output of the time averaging processing part 7 immediately after varying the frequency of the high frequency signal for the test, and it is understood that the amount of variation of a frequency can be detected in 0.1 sec or shorter. The frequency detection precision corresponds to the amplitude of the pulsation in a region where the output curve becomes parallel to the time axis after stop of increase in the output curve, and this value is 0.0035 Hz, which supports that the frequency detection precision is extremely high.

The invention claimed is:

1. A sensing instrument for detecting a substance to be detected, based on the variation of the natural frequency of a sensor oscillator, using the sensor oscillator, on the surface of which an adsorbing layer to adsorb a substance to be detected is formed, and of which natural frequency is varied by adsorption of the substance to be detected, said sensing apparatus comprising:

a sensor oscillator circuit to oscillate said sensor oscillator;

a reference clock generating part to generate a clock signal for sampling frequency signals from said sensor oscillator;

an analog/digital converting part for sampling the frequency signal from said sensor oscillator by the clock signal from said reference clock generating part, and outputting the sampling value as a digital signal;

a means for obtaining a rotational vector to obtain a real part and an imaginary part when performing a quadrature detection with a digital signal for a frequency signal corresponding to the output signal from the analog/digital converting part, and performing complex notation of the rotational vector rotating at an angular velocity corresponding to the difference of frequency between the frequency of the frequency signal and the frequency identified by the digital signal used for the quadrature detection; and a means for calculating the velocity of the rotational vector to determine the angular velocity of the rotational vector based on respective time series data of said real part and the imaginary part obtained by the means for obtaining the rotational vector.

2. The sensing instrument according to claim 1, further comprising a means for determining the difference between the angular velocity of a rotational vector when the sensor oscillator is placed under a first circumstance and the angular velocity of a rotational vector when the sensor oscillator is placed under a second circumstance.

3. The sensing instrument according to claim 1, wherein said means for obtaining the rotational vector comprises: a means for performing a quadrature detection for a frequency signal corresponding to the output signal from the analog/digital converting part; and a means for eliminating high frequency components contained in the data obtained by this means.

4. The sensing instrument according to claim 1, wherein said means for calculating the velocity of the rotational vector determines an angular velocity of the rotational vector based on the calculation of $\{Q(n)-Q(n-1)\} \cdot I(n) - \{I(n)-I(n-1) \cdot Q(n)$, when the real part and the imaginary part corresponding to said sampling value at a certain timing are taken as $I(n)$ and $Q(n)$ respectively, and a real part and an imaginary part corresponding to said sampling value at a timing earlier than the above timing are taken as $I(n-1)$ and $Q(n-1)$ respectively.

5. The sensing instrument according to claim 1, further comprising: a means for determining the average value within a prescribed period of time to the calculated result determined by said means for calculating the velocity of the rotational vector.

6. The sensing instrument according to claim 5, wherein said means for determining the average value within a prescribed period of time is a means for determining the moving average.

7. The sensing instrument according to claim 1, further comprising:

a correction processing part for performing division of said real part and the imaginary part by the scalar of the vector determined by these real part and the imaginary part, at a pre-stage of said means for calculating the velocity of the rotational vector.

8. The sensing instrument according to claim 1, further comprising:

a reversely rotational vector generating part for generating a real part and an imaginary part when displaying in complex expression of a reversely rotational vector rotating in the opposite direction to said rotational vector at the angular velocity determined by said means for calculating the velocity of the rotational vector; and a frequency range correcting part, provided at the pre-stage of said means for calculating the velocity of the rotational vector, and for compensating the range of frequency variation by retarding the angular velocity of said rotational vector by calculating the real part and the imaginary part of the rotational vector obtained by said means for obtaining the rotational vector, and the real part and the imaginary part of the reversely rotational vector generated by said reversely rotational vector generating part.

9. The sensing instrument according to claim 8, wherein the reversely rotational vector generating part comprises: a data table in which a set of the real part and the imaginary part defining the position of the reversely rotational vector on the complex plane are arranged in turn along the rotational direction; and an address controlling part for generating a reversely rotational vector by generating the address of said data table using an increment number or a decrement number corresponding to said frequency variation.

10. The sensing instrument according to claim 9, wherein the reversely rotational vector generating part comprises: a pulse width controlling part for outputting a pulse train having a duty ratio in accordance with the lower rank bit value when expressing the frequency variation obtained by said means for calculating the velocity of the rotational vector with a digital signal; and an adding part for adding the higher rank bit value when expressing said frequency variation with the digital signal and the level of the pulse formed by said pulse width controlling part to output to said address controlling part;

wherein, said address generating part integrates the output value from the adding part, and the integrated value is used as an address in said data table.

* * * * *